(12) United States Patent
Natal et al.

(10) Patent No.: US 10,159,961 B2
(45) Date of Patent: Dec. 25, 2018

(54) ALKYLENE OXIDE CATALYST AND USE THEREOF

(71) Applicants: Manuel A. W. Natal, Lake Jackson, TX (US); Madan M. Bhasin, Charleston, WV (US); Hwaili Soo, Charleston, WV (US); Albert C. Liu, Charleston, WV (US)

(72) Inventors: Manuel A. W. Natal, Lake Jackson, TX (US); Madan M. Bhasin, Charleston, WV (US); Hwaili Soo, Charleston, WV (US); Albert C. Liu, Charleston, WV (US)

(73) Assignee: Dow Global Technologies LLC, Midland, MI (US)

( * ) Notice: Subject to any disclaimer, the term of this patent is extended or adjusted under 35 U.S.C. 154(b) by 757 days.

(21) Appl. No.: 13/624,131

(22) Filed: Sep. 21, 2012

(65) Prior Publication Data
US 2014/0088316 A1 Mar. 27, 2014
US 2016/0082423 A9 Mar. 24, 2016

Related U.S. Application Data

(63) Continuation of application No. 12/297,331, filed as application No. PCT/US2007/009446 on Apr. 17, 2007, now abandoned.
(Continued)

(51) Int. Cl.
B01J 27/055 (2006.01)
C07D 301/10 (2006.01)
(Continued)

(52) U.S. Cl.
CPC ............ B01J 27/055 (2013.01); B01J 21/04 (2013.01); B01J 23/50 (2013.01); B01J 23/58 (2013.01);
(Continued)

(58) Field of Classification Search
CPC . B01J 23/48; B01J 23/66; B01J 23/688; B01J 27/055; B01J 21/04; B01J 23/50;
(Continued)

(56) References Cited

U.S. PATENT DOCUMENTS 4,994,589 A * 2/1991 Notermann ............... B01J 23/66
549/534
5,387,751 A 2/1995 Hayden et al.
(Continued)

FOREIGN PATENT DOCUMENTS

GB 2043481 * 3/1980
WO 9740933 A1 11/1997
(Continued)

OTHER PUBLICATIONS

Intellectual Property India, Patent Office Hearing Notice dated Aug. 11, 2016 for: Indian Patent Application No. 5599/CHENP/2008.

Primary Examiner — James A Fiorito

(57) ABSTRACT

A supported silver catalyst and use thereof in a process for producing an alkylene oxide, such as ethylene oxide, by the direct oxidation of an alkylene with oxygen or an oxygen-containing gas, wherein the catalyst provides improved stability and improved resilience to reactor upsets and timely recovery to substantially pre-upset levels of catalyst activity and/or efficiency. In some embodiments, the catalyst also exhibits improved activity. A catalyst capable of producing ethylene oxide at a selectivity of at least 87 percent while achieving a work rate of at least 184 kg/h/m$^3$ at a temperature of no greater than 235° C. when operated in a process where the inlet feed to a reactor containing the catalyst comprises ethylene, oxygen, and carbon dioxide, wherein the concentration of carbon dioxide in the inlet feed is greater than or equal to 2 mole percent.

12 Claims, 3 Drawing Sheets

Related U.S. Application Data

(60) Provisional application No. 60/792,712, filed on Apr. 18, 2006.

(51) Int. Cl.

| | | |
|---|---|---|
| *B01J 37/02* | (2006.01) | |
| *B01J 37/16* | (2006.01) | |
| *B01J 21/04* | (2006.01) | |
| *B01J 23/50* | (2006.01) | |
| *B01J 23/58* | (2006.01) | |
| *B01J 23/68* | (2006.01) | |
| *C07C 209/60* | (2006.01) | |
| *B01J 35/02* | (2006.01) | |
| *B01J 35/00* | (2006.01) | |

(52) U.S. Cl.
CPC .......... *B01J 23/688* (2013.01); *B01J 35/023* (2013.01); *B01J 37/0203* (2013.01); *B01J 37/0205* (2013.01); *B01J 37/0244* (2013.01); *B01J 37/16* (2013.01); *C07C 209/60* (2013.01); *C07D 301/10* (2013.01); *B01J 35/006* (2013.01); *B01J 35/0013* (2013.01); *Y02P 20/52* (2015.11)

(58) Field of Classification Search
CPC ...... B01J 23/58; B01J 35/023; B01J 37/0203; B01J 37/0205; B01J 37/0244; B01J 37/16; C07C 209/60; C07D 301/10
USPC .......................... 502/218, 347, 348, 324, 335
See application file for complete search history.

(56) References Cited

U.S. PATENT DOCUMENTS

| | | |
|---|---|---|
| 7,932,407 B2 | 4/2011 | Matusz et al. |
| 2004/0198993 A1 | 10/2004 | Matusz et al. |
| 2005/0101790 A1 | 5/2005 | Rizkalla et al. |

FOREIGN PATENT DOCUMENTS

| | | | | |
|---|---|---|---|---|
| WO | 2004078736 A1 | | 9/2004 | |
| WO | 2005023418 A1 | | 3/2005 | |
| WO | WO2008/054564 | * | 5/2008 | .............. B01J 21/04 |

\* cited by examiner

ALKYLENE OXIDE CATALYST AND USE THEREOF

CROSS-REFERENCE TO PRIOR APPLICATION

This application claims priority to and is a continuation application of U.S. application Ser. No. 12/297,331 filed Oct. 16, 2008, which claims priority to and is a 35 U.S.C. 371 national phase application of International Application No. PCT/US07/09446 filed Apr. 17, 2007, which claims the benefit of U.S. Provisional Application No. 60/792,712 filed Apr. 18, 2006.

BACKGROUND OF THE INVENTION

This invention pertains to a supported silver catalyst, its manufacture, and its use in the production of an alkylene oxide, particularly, ethylene oxide, directly from oxygen and an olefin, such as ethylene.

Alkylene oxides are known for a multiplicity of utilities. Ethylene oxide, for example, is used to produce ethylene glycol, which is used in preparing polyester fibers and resins, nonionic surfactants, glycol ethers, ethanolamines, and polyethylene polyether polyols. Propylene oxide is used to produce propylene glycol and polypropylene polyether polyols, which are used in polyurethane polymer applications.

The manufacture of ethylene oxide by the direct reaction of ethylene with oxygen or an oxygen-containing gas in the presence of a silver catalyst is an old and well developed art. An outline of the history of direct ethylene oxidation can be found in U.S. Pat. No. 4,916,243. This patent, more particularly, describes a catalyst comprising silver deposited on an alpha-alumina macroporous support, further comprising cesium and at least one other alkali metal selected from the group consisting of lithium, sodium, potassium, and rubidium, such that the combination of cesium and other alkali metals exhibits a synergistic promoting effect on the oxidation process.

A supported silver catalyst for alkylene oxide manufacture should have acceptable activity, efficiency, and stability. The "activity" of a catalyst can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reactor temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide. The "efficiency" of the oxidation, which is synonymous with "selectivity," refers to the total amount, in molar percent, of converted or reacted olefin that forms a particular product. For example, the "selectivity to alkylene oxide" refers to the percentage on a molar basis of converted or reacted olefin that forms alkylene oxide. One measure of the useful life of a catalyst is the length of time that reactants can be passed through the reaction system during which time acceptable productivity is obtained in light of all relevant factors. "Deactivation", as used herein, refers to a permanent loss of activity and/or efficiency, that is, a decrease in activity and/or efficiency that cannot be recovered. Generally, deactivation tends to proceed more rapidly when higher reactor temperatures are employed. The "stability" of a catalyst is inversely proportional to the rate of deactivation. Lower rates of deactivation are generally desirable.

In recent years, improvements in activity, efficiency, and stability of alkylene oxide catalysts have been achieved with the use of carriers comprising high-purity alpha-alumina of greater than 80 weight percent compositional purity. For example, U.S. Pat. Nos. 4,994,588 and 4,994,587 and references therein disclose carriers of high-purity alpha-alumina and methods of making them. The carriers and catalysts derived from these carriers typically do not contain binders, such as certain clays. Binders tend to introduce quantities of extraneous metals, particularly alkali metal-containing species, which may influence the performance of the catalyst prepared on those carriers. Although high purity alpha-alumina is desirable for the control of alkali metal content, other modifiers may be added to the carrier in order to improve catalyst performance. For example, WO-A1-2005/039757 discloses high-purity alpha-alumina carriers containing zirconium silicate (zircon), and EP1354626 and U.S. Pat. No. 5,145,824 describe carriers prepared with various modifier components.

The above-described references are silent regarding the effects of reactor upsets on catalyst performance. For the purposes of this invention, the term "reactor upset" shall refer to an interruption in the alkylene oxide process that may occur, for example, as a result of mechanical or electrical failure in process equipment, or shut-down due to loss of process control or external influences (e.g., detrimental weather conditions), or interruption or stoppage resulting for any reason other than normal catalyst aging. Reactor upsets may vary in duration from about a few minutes to about several months. Reactor upsets frequently present recovery problems with the catalyst. Catalyst activity and/or efficiency may not recover to pre-upset levels as quickly as desired. In fact, several weeks may elapse before catalyst activity and/or efficiency are fully recovered. Worse still, the catalyst may never recover to pre-upset levels of activity and/or efficiency, but rather may settle into lower activity and/or efficiency levels. Each reactor upset results in lost productivity; but often the effect is permanent, rather than temporary, because the catalyst fails to recover its former activity and/or efficiency.

SUMMARY OF THE INVENTION

We have now observed that deficiencies in recovery from reactor upsets are more pronounced for catalysts prepared using high-purity alpha-alumina carriers, which catalysts otherwise provide for improved activity, efficiency, and stability, as compared with catalysts prepared from lower purity alpha-alumina carriers. In view of the above, we found it desirable to discover a novel catalyst prepared with a high-purity alpha-alumina carrier for use in an ethylene oxide process, the catalyst having resilience toward recovery from a reactor upset, in an acceptable time frame, to substantially pre-upset levels of catalyst activity and/or efficiency. In addition, the catalyst exhibits increased stability as measured by aging rates for selectivity and activity. Further, when the catalyst also comprises a promoting amount of rhenium and a promoting amount of manganese, the catalyst exhibits resilience, stability, and improved activity, wherein such improved activity is at least about 3° C. under STANDARD ETHYLENE EPOXIDATION PROCESS CONDITIONS as compared with a second catalyst comprised of the same materials except that the second catalyst does not contain manganese. For purposes of this invention, the term "high-purity carrier" is defined as a carrier comprising at least about 80 weight percent alpha-alumina and comprising less than about 30 parts per million acid-leachable alkali metals by weight, the weight percent of the alpha-alumina and the concentration of the acid-leachable alkali metals being calculated on the weight of the carrier, where the acid-leachable alkali metals are selected from lithium, sodium, potassium, and mixtures thereof.

We found it more desirable to obtain such resilience and stability in such a catalyst that exhibits a high pre-upset productivity level, as measured by activity and/or efficiency. We found it even more desirable to obtain resilience, stability, and improved efficiency while operating the alkylene oxide process at a high workrate. For the purposes of this invention, the term "workrate" is defined as mass of alkylene oxide produced per unit time per unit reactor volume. A "high workrate" shall be taken to be greater than about 4 kilogram-moles alkylene oxide (AO) produced per hour per cubic meter of reactor volume (kg-mol AO/h/m$^3$).

We have found an improved process for producing ethylene oxide using a supported silver catalyst comprising deposited silver and promoters. The feed gas comprises ethylene, oxygen, and at least 2 mole % carbon dioxide. The reaction temperature is less than 240° C. at a selectivity of at least 87 percent to ethylene oxide. The concentration of ethylene oxide in the outlet stream is at least 1.5 mole percent. The work rate is at least 176 kg of ethylene oxide per m$^3$ per hour. At least a portion of the reactor outlet stream is recycled to the reactor inlet feed.

We have also discovered a catalyst capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, wherein the concentration of carbon dioxide in the inlet feed is greater than or equal to 2 mole percent.

One embodiment of the present invention is a supported silver catalyst is prepared on an alumina-containing carrier, the carrier comprising greater than about 80 weight percent alpha-alumina and less than about 30 parts per million acid-leachable alkali metals by weight, the weight percent of the alumina and the concentration of the acid-leachable alkali metals being calculated on the weight of the carrier. The acid-leachable alkali metals are selected from lithium, sodium, potassium, and mixtures thereof. Deposited on the carrier are silver; at least one first promoter selected from the group consisting of cesium, rubidium, and mixtures thereof, at least one second promoter selected from the group consisting of sodium, lithium, and mixtures thereof, and optionally, one or more additional solid promoters. The deposited sodium, if employed, is present in a concentration from about 10 ppm to about 250 ppm, and the deposited lithium, if employed, is present in a concentration from about 10 ppm to about 500 ppm by weight. The concentrations of the deposited sodium and lithium are calculated on the weight of the catalyst.

In a second embodiment of the present invention, the supported silver catalyst is prepared on an alumina-containing carrier, the carrier comprising greater than about 90 percent alpha-alumina and less than about 30 ppm acid-leachable alkali metals by weight, the weight percent of the alumina and the concentration of the acid-leachable alkali metals being calculated on the weight of the carrier. The acid-leachable alkali metals are selected from lithium, sodium, potassium, and mixtures thereof. Deposited on the carrier are silver in an amount greater than about 25 weight percent, based on the weight of the catalyst; cesium in an amount from about 0.005 to about 0.30 percent by weight, sodium in an amount from about 10 ppm to about 200 ppm by weight, and optionally, one or more additional solid promoters. The amounts of the deposited cesium and sodium are calculated on the weight of the catalyst.

In a third embodiment of the present invention, the supported silver catalyst is prepared on an alumina-containing carrier, the carrier comprising greater than about 90 percent alpha-alumina and less than about 30 ppm acid-leachable alkali metals by weight, the weight percent of the alumina and the concentration of the acid-leachable alkali metals being calculated on the weight of the carrier. The acid-leachable alkali metals are selected from lithium, sodium, potassium, and mixtures thereof. Deposited on the carrier are silver in an amount greater than about 25 weight percent, based on the weight of the catalyst; cesium in an amount from about 0.005 to about 0.30 percent by weight, lithium in an amount from about 10 ppm to about 100 ppm by weight, and optionally, one or more additional solid promoters. The amounts of the deposited cesium and lithium are calculated on the weight of the catalyst.

In a fourth embodiment of the present invention, the supported silver catalyst is prepared on an alumina-containing carrier, the carrier comprising greater than about 95 percent alpha-alumina and less than about 30 ppm acid-leachable alkali metals by weight, the weight percent of the alumina and the concentration of the acid-leachable alkali metals being calculated on the weight of the carrier. The acid-leachable alkali metals are selected from lithium, sodium, potassium, and mixtures thereof. Deposited on the carrier are silver in an amount greater than about 25 weight percent, based on the weight of the catalyst; cesium in an amount from about 200 ppm to about 1200 ppm by weight; sodium in an amount from about 10 ppm to about 150 ppm by weight; lithium in an amount from about 10 ppm to about 100 ppm by weight, and optionally, one or more additional solid promoters. The amounts of the deposited cesium, sodium and lithium are calculated on the weight of the catalyst.

In a fifth embodiment of the present invention, the supported silver catalyst consists essentially of an alpha-alumina carrier consisting essentially of greater than about 98 percent alpha-alumina and less than about 30 ppm acid-leachable lithium, sodium, and potassium by weight. The weight percent of the alumina and the concentration of the acid-leachable alkali metals are calculated on the weight of the carrier. Deposited on the carrier are silver in an amount greater than about 25 percent by weight, based on the weight of the catalyst; cesium in an amount from about 200 ppm to about 1200 ppm by weight; sodium in an amount from about 10 ppm to about 150 ppm by weight; lithium in an amount from about 10 ppm to about 100 ppm by weight; manganese in an amount from about 20 ppm to about 200 ppm by weight. The amounts of the deposited cesium, sodium, lithium, and manganese are calculated on the weight of the catalyst. Further deposited on the carrier is a promoting amount of a sulfur compound, and, optionally, rhenium, tungsten, molybdenum, or combinations thereof, wherein the ratio of 2(moles sulfur plus moles tungsten plus moles molybdenum) plus moles rhenium divided by the total moles cesium and sodium [(2(S+W+Mo)+Re)/(Cs+Na)] ranges from greater than about 0.5/1 to about 1.5/1.

In one embodiment, the amount of deposited sodium is at least about 30 ppm. In another embodiment, the amount of deposited sodium is least about 25 ppm. In one embodiment, the amount of deposited lithium is at least about 15 ppm. In another embodiment, the amount of deposited lithium is at least about 13 ppm.

In one embodiment, the supported silver catalyst further comprises a promoting amount of a sulfur compound and, optionally, rhenium, tungsten, molybdenum, or combinations thereof, wherein the ratio of 2(moles sulfur plus moles tungsten plus moles molybdenum) plus moles rhenium divided by the total moles cesium and sodium [(2(S+W+Mo)+Re)/(Cs+Na)] ranges from greater than about 0.5/1 to about 1.5/1.

In one embodiment, the first promoter is cesium and the second promoter is sodium. In another embodiment, the supported silver catalyst comprises a synergistic combination of cesium and sodium. In still another embodiment, the first promoter is cesium and the second promoter is lithium. In another embodiment, the supported silver catalyst comprises a synergistic combination of cesium and lithium. In one embodiment, the second promoter is a mixture of sodium and lithium, and the catalyst comprises a synergistic combination of cesium, sodium, and lithium.

In one embodiment, the first promoter is cesium in a concentration ranging from about 0.005 to about 0.30 weight percent, calculated on the weight of the catalyst. In another embodiment, the supported silver catalyst further comprises a promoting amount of rhenium. In another embodiment, the supported silver catalyst further comprises a promoter selected from compounds of sulfur, molybdenum, tungsten, and mixtures thereof.

In yet another embodiment, the supported silver catalyst comprises a promoting amount of manganese. In one embodiment, the amount of manganese is at least about 1.5 micromoles per gram of catalyst.

In one embodiment, the supported silver catalyst exhibits improved activity of at least about 3° C. under STANDARD ETHYLENE EPOXIDATION PROCESS CONDITIONS as compared with a second supported silver catalyst comprised of the same materials except that the second catalyst does not contain manganese. In another embodiment, the supported catalyst, when used in a process for the oxidation of alkylene with oxygen to form an alkylene oxide, is capable of achieving an efficiency of greater than about 75 percent alkylene oxide at a workrate of greater than about 4 kg-mol alkylene oxide/h/m³ of catalyst. In still another embodiment, the supported catalyst, when used in a process for the oxidation of alkylene in the presence of oxygen to form an alkylene oxide, and when subjected to a reactor upset, is capable of recovering to greater than about 80 percent of the pre-upset activity and/or efficiency in about 3 days or less. In one embodiment, the supported catalyst has increased catalyst stability as compared to a second supported silver catalyst comprised of the same materials except that the second catalyst does not contain at least one second promoter selected from the group consisting of sodium, lithium, and mixtures thereof.

In one embodiment, the alumina-containing support comprises particles of alpha-alumina each of which has at least one substantially flat major surface having a lamellate or platelet morphology which approximates the shape of a hexagonal plate, at least 50 percent of which (by number) have a major dimension of less than about 50 microns.

In one embodiment, the invention comprises a process for producing a supported silver catalyst by providing an alumina-containing carrier, the carrier comprising greater than about 80 weight percent alpha-alumina and less than about 30 parts per million acid-leachable alkali metals by weight, the weight percent of the alumina and the concentration of the acid-leachable alkali metals being calculated on the weight of the carrier, wherein the acid-leachable alkali metals are selected from lithium, sodium, potassium, and mixtures thereof. Silver, at least one first promoter selected from the group consisting of cesium, rubidium, and mixtures thereof, at least one second promoter selected from the group consisting of sodium, lithium, and mixtures thereof, and optionally, one or more additional solid promoters are deposited on the carrier.

The deposited sodium, if employed, is present in a concentration from about 10 ppm to about 250 ppm, and wherein the deposited lithium, if employed, is present in a concentration from about 10 ppm to about 500 ppm by weight, the concentrations of the deposited sodium and lithium being calculated on the weight of the catalyst.

The invention also comprises a continuous process for the production of alkylene oxide comprising contacting in a vapor phase an alkylene with oxygen or an oxygen-containing gas in the presence of a supported silver catalyst. The contacting is conducted under process conditions sufficient to produce the alkylene oxide, and the supported silver catalyst is one of the supported silver catalysts of the present invention. In one embodiment, the process exhibits improved activity of at least about 3° C. as compared with a process using second supported silver catalyst comprised of the same materials except that the second catalyst does not contain manganese.

In one embodiment, the process is for the production of ethylene oxide.

In one embodiment, the invention provides a catalyst comprising silver and promoters deposited on a support comprising alpha-alumina. The catalyst is capable of producing ethylene oxide at a selectivity of at least 87 percent while achieving a work rate of at least 184 kg/h/m³ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. In one embodiment, this catalyst is capable of producing ethylene oxide at a selectivity of at least 87 percent while achieving a work rate of at least 184 kg/h/m³ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. The process is operated at a reactor pressure of no greater than 2275 kPa, absolute, and a space velocity of no greater than 4700 h⁻¹. The concentration of ethylene in the inlet feed is less than or equal to 25 mole percent, and the concentration of oxygen in the inlet feed is less than or equal to 8 mole percent. In one embodiment, this catalyst is capable of producing ethylene oxide at a selectivity of at least 87 percent while achieving a work rate of at least 184 kg/h/m³ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. The process is operated at a reactor pressure of no greater than 2275 kPa, absolute, and a space velocity of no greater than 4700 h$^{-1}$. The concentration of ethylene in the inlet feed is less than or equal to 25 mole percent, the concentration of oxygen in the inlet feed is less than or equal to 8 mole percent, the inlet feed further comprises one or more chlorine-containing reaction modifier species, and the concentration of chlorine-containing reaction modifier species in the inlet feed is such that the selectivity towards ethylene oxide formation is optimal. In one embodiment, this catalyst, at a cumulative ethylene oxide production of at least 0.32 kT ethylene oxide per m$^3$ of catalyst, is capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. The process is operated at a reactor pressure of no greater than 2275 kPa, absolute, and a space velocity of no greater than 4700 h$^{-1}$. The concentration of ethylene in the inlet feed is less than or equal to 25 mole percent, and the concentration of oxygen in the inlet feed is less than or equal to 8 mole percent. The inlet feed further comprises one or more chlorine-containing reaction modifier species, and the concentration of chlorine-containing reaction modifier species in the inlet feed is such that the selectivity towards ethylene oxide formation is optimal. In one embodiment, this catalyst, at a cumulative ethylene oxide production of at least 0.32 kT ethylene oxide per m$^3$ of catalyst, is capable of producing ethylene oxide at a selectivity of at least 87.5 percent while achieving a work rate of at least 184 kg/h/m3 at a temperature of no greater than 231° C. when operated in a process using a reactor containing a catalyst, the reactor being provided with an inlet feed and having withdrawn therefrom an outlet stream, where the inlet feed to the reactor comprises ethylene, oxygen, carbon dioxide and one or more chlorine-containing reaction modifier species. The process is operated at a reactor pressure of no greater than 2275 kPa, absolute, and a space velocity of no greater than 4700 h$^{-1}$. The concentration of ethylene in the inlet feed is less than or equal to 25 mole percent, the concentration of oxygen in the inlet feed is less than or equal to 8 mole percent, the concentration of carbon dioxide in the inlet feed is greater than or equal to 2 mole percent, and the concentration of chlorine-containing reaction modifier species in the inlet feed is such that the selectivity towards ethylene oxide formation is optimal.

In another embodiment, the invention provides a catalyst comprising an alpha-alumina carrier having a purity of at least 95 weight percent alpha-alumina. Deposited on the carrier are silver, at least one first promoter selected from the group consisting of cesium, rubidium, and mixtures thereof, at least one second promoter selected from the group consisting of sodium, lithium, and mixtures thereof, a promoting amount of rhenium, and at least one rhenium co-promoter selected from compounds of sulfur, molybdenum, tungsten, and mixtures thereof. The catalyst is capable of producing ethylene oxide at a selectivity of at least 87 percent while achieving a work rate of at least 184 kg/h/m$^3$ at a temperature of no greater than 240° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent and at least a portion of the carbon dioxide has been recycled from the outlet stream of the reactor. In one embodiment, the catalyst is capable of producing ethylene oxide at a selectivity of at least 87 percent while achieving a work rate of at least 184 kg/h/m$^3$ at a temperature of no greater than 240° C. when operated in a process using a reactor containing a catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent and at least a portion of the carbon dioxide has been recycled from the outlet stream of the reactor. The process is operated at a reactor pressure of no greater than 2275 kPa, absolute, and a space velocity of no greater than 4700 h$^{-1}$. The concentration of ethylene in the inlet feed is less than or equal to 25 mole percent, and the concentration of oxygen in the inlet feed is less than or equal to 8 mole percent. In one embodiment, the catalyst is capable of producing ethylene oxide at a selectivity of at least 87 percent while achieving a work rate of at least 184 kg/h/m$^3$ at a temperature of no greater than 240° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent and at least a portion of the carbon dioxide has been recycled from the outlet stream of the reactor. The process is operated at a reactor pressure of no greater than 2275 kPa, absolute, and a space velocity of no greater than 4700 h$^{-1}$. The concentration of ethylene in the inlet feed is less than or equal to 25 mole percent, the concentration of oxygen in the inlet feed is less than or equal to 8 mole percent, the inlet feed further comprises one or more chlorine-containing reaction modifier species, and the concentration of chlorine-containing reaction modifier species in the inlet feed is such that the selectivity towards ethylene oxide formation is optimal.

In another embodiment, this catalyst at a cumulative ethylene oxide production of at least 0.32 kT ethylene oxide per m$^3$ of catalyst, is capable of producing ethylene oxide at a selectivity of at least 87 percent while achieving a work rate of at least 184 kg/h/m$^3$ at a temperature of no greater than 240° C. when operated in a process using a reactor containing the catalyst, the reactor being provided with an inlet feed and having withdrawn therefrom an outlet stream, where the inlet feed to the reactor comprises ethylene, oxygen, and carbon dioxide, the concentration of carbon dioxide in the inlet feed is greater than or equal to 2 mole percent and at least a portion of the carbon dioxide has been recycled from the outlet stream of the reactor. The process is operated at a reactor pressure of no greater than 2275 kPa, absolute, and a space velocity of no greater than 4700 h$^{-1}$. The concentration of ethylene in the inlet feed is less than or equal to 25 mole percent, the concentration of oxygen in the inlet feed is less than or equal to 8 mole percent, the inlet feed further comprises one or more chlorine-containing reaction modifier species, and the concentration of chlorine-containing reaction modifier species in the inlet feed is such that the selectivity towards ethylene oxide formation is optimal. In one embodiment, this catalyst, at a cumulative ethylene oxide production of at least 0.32 kT ethylene oxide per m$^3$ of catalyst, is capable of producing ethylene oxide at a selectivity of at least 87.5 percent while achieving a work rate of at least 184 kg/h/m3 at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, carbon dioxide and one or more chlorine-containing reaction modifier species. The process is operated at a reactor pressure of no greater than 2275 kPa, absolute, and a space velocity of no greater than 4700 $h^{-1}$. The concentration of ethylene in the inlet feed is less than or equal to 25 mole percent, the concentration of oxygen in the inlet feed is less than or equal to 8 mole percent, the concentration of carbon dioxide in the inlet feed is greater than or equal to 2 mole percent and at least a portion of the carbon dioxide has been recycled from the outlet stream of the reactor, and the concentration of chlorine-containing reaction modifier species in the inlet feed is such that the selectivity towards ethylene oxide formation is optimal.

In still another embodiment, the invention provides a catalyst comprising an alpha-alumina carrier having a purity of at least 95 weight percent alpha-alumina. Deposited on the silver are at least one first promoter selected from the group consisting of cesium, rubidium, and mixtures thereof, at least one second promoter selected from the group consisting of sodium, lithium, and mixtures thereof, a promoting amount of rhenium, and at least one rhenium co-promoter selected from compounds of sulfur, molybdenum, tungsten, and mixtures thereof. The catalyst is capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. In one embodiment, this catalyst is capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, and the concentration of carbon dioxide in the inlet feed is greater than or equal to 2 mole percent. The process is operated at a reactor pressure of no greater than 2275 kPa, absolute, and a space velocity of no greater than 4700 $h^{-1}$. The concentration of ethylene in the inlet feed is less than or equal to 25 mole percent and the concentration of oxygen in the inlet feed is less than or equal to 8 mole percent. In another embodiment, this catalyst is capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, the concentration of carbon dioxide in the inlet feed is greater than or equal to 2 mole percent. The process is operated at a reactor pressure of no greater than 2275 kPa, absolute, and a space velocity of no greater than 4700 $h^{-1}$. The concentration of ethylene in the inlet feed is less than or equal to 25 mole percent, the concentration of oxygen in the inlet feed is less than or equal to 8 mole percent, the inlet feed further comprises one or more chlorine-containing reaction modifier species, and the concentration of chlorine-containing reaction modifier species in the inlet feed is such that the selectivity towards ethylene oxide formation is optimal.

In another embodiment, this catalyst, at a cumulative ethylene oxide production of at least 0.32 kT ethylene oxide per m$^3$ of catalyst, is capable of producing ethylene oxide at a selectivity of at least 87 percent while achieving a work rate of at least 184 kg/h/m$^3$ at a temperature of no greater than 235° C. when operated in a process using a reactor containing the catalyst, the reactor being provided with an inlet feed and having withdrawn therefrom an outlet stream, where the inlet feed to the reactor comprises ethylene, oxygen, and carbon dioxide, the concentration of carbon dioxide in the inlet feed is greater than or equal to 2 mole percent. The process is operated at a reactor pressure of no greater than 2275 kPa, absolute, and a space velocity of no greater than 4700 $h^{-1}$. The concentration of ethylene in the inlet feed is less than or equal to 25 mole percent, the concentration of oxygen in the inlet feed is less than or equal to 8 mole percent, the inlet feed further comprises one or more chlorine-containing reaction modifier species, and the concentration of chlorine-containing reaction modifier species in the inlet feed is such that the selectivity towards ethylene oxide formation is optimal. In one embodiment, this catalyst, at a cumulative ethylene oxide production of at least 0.32 kT ethylene oxide per m$^3$ of catalyst, is capable of producing ethylene oxide at a selectivity of at least 87.5 percent while achieving a work rate of at least 184 kg/h/m3 at a temperature of no greater than 231° C. when operated in a process using a reactor containing the catalyst, the reactor being provided with an inlet feed and having withdrawn therefrom an outlet stream, where the inlet feed to the reactor comprises ethylene, oxygen, carbon dioxide and one or more chlorine-containing reaction modifier species. The process is operated at a reactor pressure of no greater than 2275 kPa, absolute, and a space velocity of no greater than 4700 $h^{-1}$. The concentration of ethylene in the inlet feed is less than or equal to 25 mole percent, the concentration of oxygen in the inlet feed is less than or equal to 8 mole percent, the concentration of carbon dioxide in the inlet feed is greater than or equal to 2 mole percent, and the concentration of chlorine-containing reaction modifier species in the inlet feed is such that the selectivity towards ethylene oxide formation is optimal.

In another embodiment, the catalyst further comprises a promoting amount of manganese.

The present invention further includes a process for producing ethylene oxide comprising contacting a reactor feed comprising ethylene, oxygen, and carbon dioxide with a catalyst bed comprising any one or more of the foregoing catalysts. In one embodiment of the process, the concentration of carbon dioxide in the reactor feed is greater than or equal to 2 mole percent. In one embodiment of the process, the reactor feed further comprises one or more chlorine-containing reaction modifier species, and the concentration of the chlorine-containing reaction modifier species in the reactor feed is such that the selectivity towards ethylene oxide formation is optimal.

In one embodiment, the invention includes a process for producing ethylene oxide using a supported silver catalyst comprising deposited silver and promoters. The feed gas comprises ethylene, oxygen, and at least 2 mole % carbon dioxide. The reaction temperature is less than 240° C. at a selectivity of at least 87 percent to ethylene oxide. The concentration of ethylene oxide in the outlet stream is at least 1.5 mole percent. The work rate is at least 176 kg of ethylene oxide per m³ per hour. At least a portion of the reactor outlet stream is recycled to the reactor inlet feed.

The present invention also includes producing an ethylene glycol, an ethylene amine, or an ethylene glycol ether by converting the ethylene oxide produced by any of the processes described above.

DRAWINGS

Figure 1:
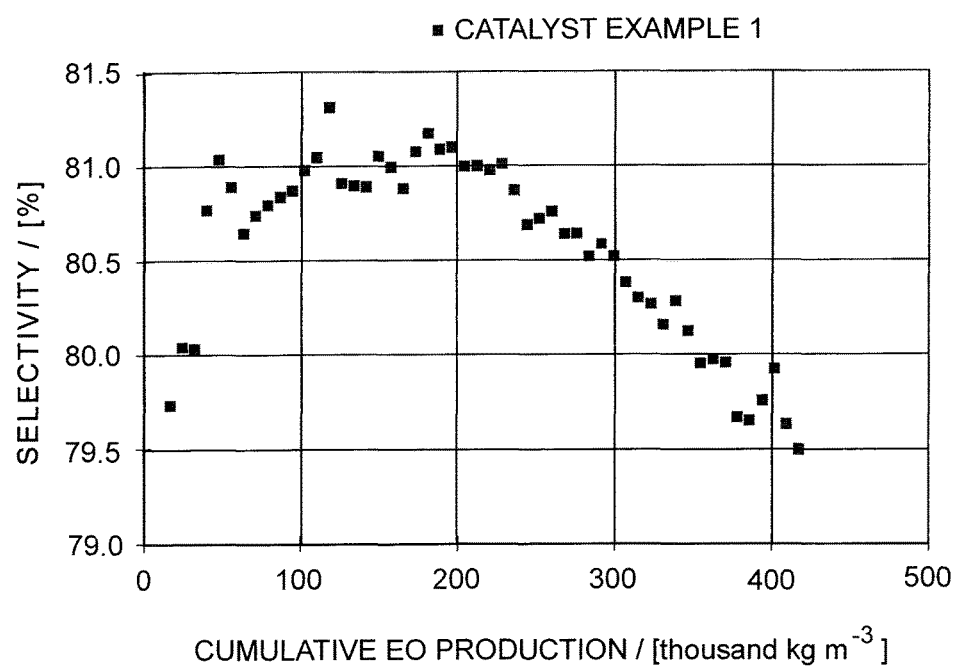
FIG. 1 illustrates a graph of ethylene oxide efficiency (selectivity) as a function of cumulative ethylene oxide production for a catalyst of this invention.
Figure 2:
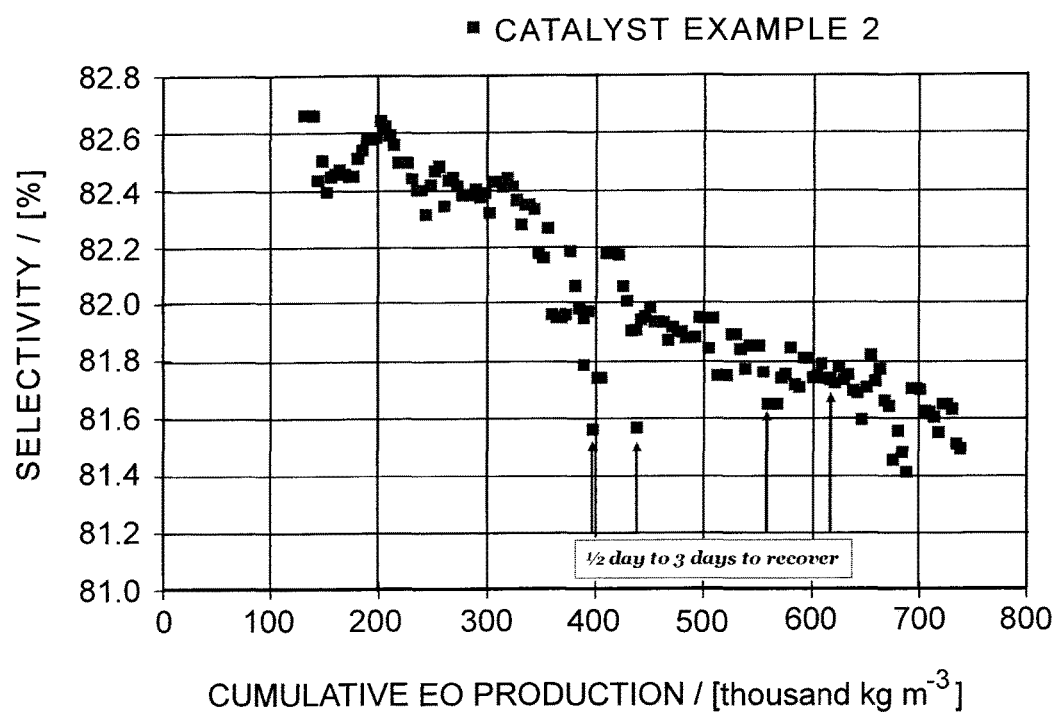
FIG. 2 illustrates a graph of ethylene oxide efficiency for a catalyst of this invention as a function of cumulative ethylene oxide production before, after, and throughout a period of several process upsets.
Figure 3:
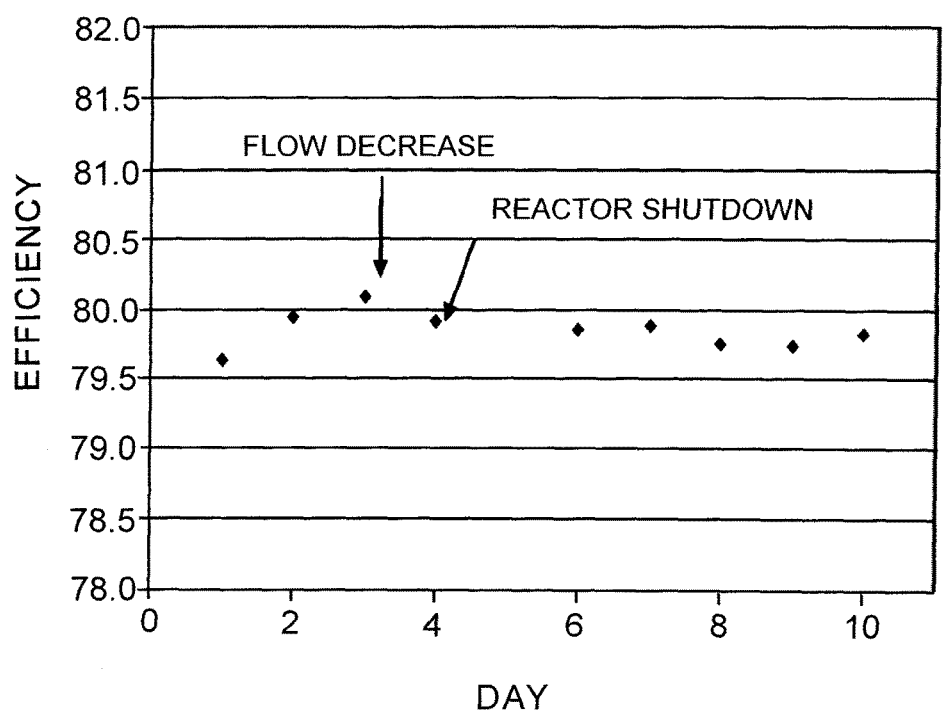
FIG. 3 illustrates a graph of the ethylene oxide efficiency for a catalyst of this invention as a function of cumulative ethylene oxide production before, after, and throughout a process upset.

Each data point in FIGS. 1, 2, and 3 represents a daily average of the catalyst performance.

DETAILED DESCRIPTION OF THE INVENTION

The invention described herein provides for a novel supported silver catalyst which finds utility in the direct oxidation of an alkylene (olefin), such as ethylene, with oxygen or an oxygen-containing gas to form an alkylene oxide, such as ethylene oxide, and which exhibits resilience when challenged with a reactor upset. As used herein, the words "resilience" and "resilient" are synonymous, and both indicate a timely recovery from reactor upsets, specifically, a recovery within about ½ day to about 3 days from start-up after an upset, to substantially pre-upset levels of catalyst activity and/or efficiency. For the purposes of this invention, a "pre-upset level of activity" means an average of the activity (for example, reaction temperature at a fixed EO concentration in the outlet gas) over a period of steady operation prior to the upset. A "pre-upset level of efficiency" means an average of the efficiency over a period of steady operation prior to the upset. Typically, a period of steady operation is about 48 hours under substantially constant process conditions, although other time frames may be equally appropriate. Normally, the steady operation occurs after the catalyst has been fully activated. "After the catalyst has been fully activated" refers to a catalyst that after an initial activation period exhibits a normal catalyst aging profile. Such a catalyst has essentially reached, and is essentially no longer reaching towards or approaching, its normal activity profile for the process conditions chosen. As used herein, "stability" is defined by aging rates for selectivity and activity. A plot of selectivity versus cumulative ethylene oxide production at a constant ethylene oxide production rate is prepared, and the slope (first derivative) of the plot is calculated to provide the selectivity aging rate. A plot of inlet coolant temperature versus cumulative ethylene oxide production at a constant ethylene oxide production rate is prepared, and the slope (first derivative) of the plot is calculated to provide the activity aging rate. Alternatively, time on stream instead of cumulative ethylene oxide production may be used. The aging rate is calculated after the catalyst has been fully activated. An improvement is demonstrated by a lower absolute value of the slope or the first derivative. Other temperature measurements such as, but not limited to, temperature of the catalyst bed, outlet gas temperature, and peak gas temperature may also be used to generate plots to calculate the activity aging rate. The inlet coolant temperature is the temperature of the coolant at about the point where the process gas enters the reactor; it correlates positively with the average temperature of the process gas. The inlet coolant temperature is also known as the "top shell" temperature.

Catalyst stability measurements may be made at any scale, such as laboratory scale (such as with laboratory continuous stirred tank reactors or microreactors), at pilot plant scale or commercial plant scale. The aging rates of the catalysts may be measured by actual time or accelerated aging protocols.

When determining an increase in activity or selectivity, the process and catalyst should be under steady state conditions, and the increase in activity or selectivity can often be ascertained promptly upon steady state conditions being achieved. As used herein, the increase in activity and efficiency both refer to performance achieved after a catalyst has been fully activated but before it experiences significant losses due to aging.

Alkylenes (olefins) employed in the process of this invention are preferably characterized by the following structural formula I:

(I)

wherein $R^1$ and $R^2$ are each individually selected from hydrogen and lower monovalent alkyl radicals, preferably, $C_{1-6}$ alkyl radicals, such as, methyl, ethyl, propyl, butyl, and higher homologues up to six carbon atoms. Preferably, $R^1$ and $R^2$ are each individually selected from hydrogen, methyl, and ethyl. More preferably, each $R^1$ and $R^2$ is hydrogen, and the preferred olefin is ethylene. The corresponding alkylene oxides produced in the process of this invention are preferably characterized by the following structural formula II:

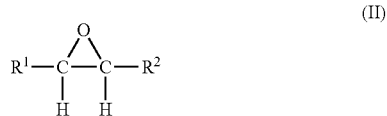

(II)

wherein $R^1$ and $R^2$ are identified hereinbefore in connection with the reactant olefin. Most preferably, the alkylene oxide is ethylene oxide.

As known from the prior art, oxygen may be provided to the process as pure molecular oxygen, or alternatively, as an oxygen-containing gas, wherein the gas further contains one or more gaseous components, for example, gaseous diluents, such as nitrogen, helium, methane, and argon, which are essentially inert with respect to the oxidation process. A suitable oxygen-containing gas, for example, is air. Additionally, the oxygen-containing gas may contain one or more of the following gaseous components including water, carbon dioxide, and various gaseous promoters and/or gaseous by-product inhibitors as discussed hereinafter.

The relative volumetric ratio of alkylene to oxygen in the feed gas may range in accordance with any of such known conventional values. Typically, the volumetric ratio of alkylene to oxygen in the feed may vary from about 2/1 to about 6/1. Likewise, the quantity of inert gases, diluents, or other gaseous components, such as water, carbon dioxide, gaseous promoters and gaseous by-product inhibitors, may vary in accordance with known conventional ranges as found in the art.

The catalyst carrier employed in practicing the invention may be selected from any of the known high purity alumina carriers, modified or unmodified. The high-purity alumina compositionally comprises greater than about 80, preferably, greater than about 90, more preferably, greater than about 95, and most preferably at least about 98 weight percent alpha-alumina. The compositional balance of the carrier typically comprises any of zirconium silicate (zircon), other refractory silicates, silica, or other metal oxides. As a necessary condition, the high-purity alpha-alumina carrier should contain less than about 30 ppm, preferably, less than about 25 ppm, and more preferably, less than about 20 ppm, acid-leachable alkali metals by weight, the concentration of the acid-leachable alkali metals being calculated on the weight of the carrier, wherein the acid-leachable alkali metals are selected from lithium, sodium, potassium, and mixtures thereof. No limits are placed on the method in which the low levels of acid-leachable alkali metals (Li, Na, K) forming a compositional part of the high-purity alpha-alumina carrier are incorporated into the carrier, if the alkalis are present at all. Typically, these acid-leachable alkali metals are introduced into the carrier during its synthesis; but other methods of introducing low levels of these acid-leachable alkali metals may be possible. What is important is that the catalyst of this invention is prepared starting from a pre-formed high-purity alpha-alumina carrier having less than about 30 ppm acid-leachable alkali metals selected from lithium, sodium, potassium, and mixtures thereof. Thereafter, the pre-formed high-purity alpha-alumina carrier is treated so as to deposit, i.e., add thereto, a first promoter chosen from cesium, rubidium, or mixtures thereof, and at least a second promoter selected from sodium, lithium and mixtures thereof. The amounts of promoters referred to as "deposited" are the total measurable amounts of such promoter added to the pre-formed carrier, regardless of its source and regardless of whether or not the amount is deliberately added. For example, those of skill in the art will recognize that certain impurities may be present in the materials used to prepare a catalyst.

Suitable shapes for the high-purity alpha-alumina carrier include any of the wide variety of shapes known for such carriers or supports, including, pills, chunks, tablets, pieces, pellets, rings, spheres, wagon wheels, toroids having star shaped inner and/or outer surfaces, and the like, of a size suitable for employment in fixed bed reactors. Conventional commercial fixed bed ethylene oxide reactors are typically in the form of a plurality of parallel elongated tubes (in a suitable shell) about 1 to 3 inches (2.5 to 7.5 cm) outer diameter and about 15 to 45 feet (4.5 to 13.5 m) long filled with catalyst. In such fixed bed reactors, it is desirable to employ a carrier formed into a rounded shape, such as, for example, spheres, pellets, rings, tablets, and the like, having diameters from about 0.1 inch (0.25 cm) to about 0.8 inch (2 cm).

There are many well-known methods of preparing alpha-alumina carriers suitable for use in alkylene oxide catalysts of the present invention. Some of such methods are described, for example, in international patent application publications WO-A1-2005/023417 and WO-A1-2005/039757; and in U.S. Pat. No. 4,994,587; U.S. Pat. No. 4,994,588; and U.S. Pat. No. 5,504,053, each of which is incorporated herein by reference.

The high-purity carrier materials may be prepared by any conventional method of removing alkali metals from a solid, particularly mineral or mineral-type material suitable in other respects as a support material. Such treatment should not, however, substantially adversely affect the mechanical or structural characteristics of the support material nor chemically alter the support material in a manner which adversely affects the catalytic performance indices of efficiency, activity, or catalyst stability. Typically, the techniques involve extraction and/or volatilization of the alkali present. A suitable extraction procedure may involve conversion of the alkali present to a more easily extractable material either in the same step in which extraction takes place or in separate conversion and extraction steps. A suitable volatilization procedure typically includes an initial step in which the alkali present in the support is converted to a material which is volatile upon heating. In some instances, it may be preferable to initially extract as much of the alkali present as possible, followed by a volatilization procedure to remove residual alkali. Exemplary of extraction or leaching procedures is treatment of the support material with a mineral acid, particularly nitric acid in a concentration of about 10 percent, by volume, at a temperature of about 90° C., for a period of about 1 hour and thereafter washing the support with water. The rinsed support material is then dried at a temperature of from about 100 to 1,000° C. for a period of from about 1 to about 3 hours.

Alternatively, suitable alpha-alumina support materials may be prepared so as to obtain alkali concentrations below 50 ppm by the method described by Weber et al in U.S. Pat. No. 4,379,134, incorporated herein by reference.

A preferred procedure for preparing a high-purity alpha-alumina support involves treatment of a support material, particularly gamma-alumina, with an organic or inorganic fluorine-containing substance, preferably in aqueous solution, and thereafter firing the treated support material at a suitable temperature. In the present invention, the support material may either be extruded by conventional techniques known to the art and formed into pellets after fluorine treatment and before firing or, alternatively, formed, e.g., extruded, pellets may be fluorine-treated and then fired. The fluorine-containing substance is, preferably, a volatile material or one which can be readily volatilized under firing conditions. Examples of suitable fluorine-containing materials include aluminum trifluoride, ammonium fluoride, hydrofluoric acid, and dichlorodifluoromethane. The fluorine compound is used in an amount sufficient to remove a major portion of the alkali present in the sample. This amount will, of course, vary with the amount of alkali present in the sample but will also depend on other factors, such as the condition under which the support material is treated, such as the firing temperature and heating rate, as well as the depth of the bed of material being treated, the amount of gamma-alumina being treated, the level of contamination of the gamma-alumina, and how well the firing chamber is sealed. Typically, a suitable amount of fluorine compound is not more than about 3 percent, by weight, based on the weight of the support material being treated. Preferably, the fluorine compound is present in an amount of about 0.8 to about 2 percent, by weight. A suitable firing temperature for fluorine-treated alumina is generally less than about 1,200° C., preferably from a temperature over 750 to about 1,100° C. The rate of heating depends in part on the amount of fluorine compound used. Thus, with lower levels of fluorine, support materials having desirable properties are generally obtained with rapid heating. As used herein, "rapid heating" refers to heating from room temperature to the desired temperature in about 1 hour. However, with lower concentrations of fluorine compound, slower heating rates are generally preferred to achieve the same type of product. The "slow heating" treatments generally consist of heating from room temperature to about 750° C. in about 0.5 to 1 hour and from 750° C. to the final temperature at a rate of about 100° C. per hour. The treatment of support materials with fluorine-containing substances may provide a collateral benefit in converting the support material to one having a preferred "platelet" morphology.

Alumina carriers which may be treated to obtain suitably high purities are also available on request, for example, from Saint-Gobain NorPro Corp., Akron, Ohio, Süd Chemie, Inc., Louisville, Ky., and Noritake Co., Limited, Nagoya 451-8501 Japan.

Preferably, an alpha-alumina support of at least 80 percent purity having desirable properties (such as, desirable morphology, surface area, pore volume, and/or pore size distribution) can be prepared by compounding (mixing) the raw material, extruding, drying, and high-temperature calcining. In this case, the raw material usually includes one or more alumina powder(s) with different properties, and may include, optionally, a material that provides for physical strength, and optionally, a burnout material (usually an organic compound) used to provide desired porosity after removal by calcination, provided that the binder and burnout material do not add a quantity of alkali metal (Li, Na, K) to the carrier beyond the required upper limit of less than about 30 ppm by weight acid-leachable alkali metals. The levels of impurities in the finished carrier are determined by the purity of the raw materials used, their degree of volatilization during the calcination step, and whether or not they are removed in post-calcination treatments such as washing. Common impurities include silica, alkali and/or alkaline earth metal oxides, and trace amounts of metal and/or non-metal containing additives.

Another preferred method for preparing high-purity alpha-alumina having suitable properties comprises mixing boehmite alumina (AlOOH) and/or gamma-alumina with an optional modifier, peptizing the boehmite alumina in an acidic mixture containing halide anions (preferably fluoride anions) to provide halogenated alumina; forming (for example, by extruding or pressing) the peptized halogenated alumina to provide formed peptized halogenated alumina; drying the formed peptized halogenated alumina to provide dried formed alumina; and calcining the dried formed alumina to provide pills of alpha-alumina carrier.

The high-purity alpha-alumina carrier prepared as described hereinabove preferably has a specific surface area of at least about 0.5 $m^2/g$, and more preferably, at least about 0.7 $m^2/g$. The surface area is typically less than about 10 $m^2/g$, and preferably, less than about 5 $m^2/g$. The high-purity alumina carrier preferably has a pore volume of at least about 0.5 $cm^3/g$, and more preferably, from about 0.5 $cm^3/g$ to about 2.0 $cm^3/g$; and a median pore diameter from about 1 to about 50 microns. Preferably, the formed high-purity alpha-alumina has a crush strength of greater than about 1 pound per 1 millimeter in pill length. The high-purity alpha-alumina preferably includes particles each of which has at least one substantially flat major surface having a lamellate or platelet morphology which approximates the shape of a hexagonal plate (some particles having two or more flat surfaces), at least 50 percent of which (by number) have a major dimension of less than about 50 microns.

In a preferred embodiment, the alpha-alumina carrier comprises zirconium silicate (zircon), present substantially as zirconium silicate in the finished carrier, more preferably, in an amount up to about 4 weight percent, calculated on the weight of the carrier.

Catalysts of this invention for the production of alkylene oxide, for example, ethylene oxide or propylene oxide, may be prepared with the aforementioned high-purity alpha-alumina, by impregnating the carrier with a solution of one or more silver compounds, as is well known in the art. The one or more first promoters (Cs, Rb, or mixtures thereof) and a second promoters selected from the group consisting of sodium, lithium, and mixtures thereof may be impregnated simultaneously with the silver impregnation, or before the silver impregnation, or after the silver impregnation or in different impregnations from each other.

The art discloses the concept of "promoters," that is, materials which, when present in combination with the catalytic silver, benefit one or more aspects of catalyst performance or otherwise act to promote the catalyst's ability to make a desired alkylene oxide product, preferably, ethylene oxide or propylene oxide. Such promoters in themselves are generally not considered catalytic materials; however, the presence of such promoters in the catalyst has been shown to contribute to one or more beneficial effects on the catalyst performance, for example, enhancing the rate or amount of production of desired product (for example, by enhancing activity and/or efficiency), reducing the temperature required to achieve a suitable rate of reaction, and/or reducing the rates or amounts of undesired by-product reactions. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, in this case alkylene oxide, and more preferably, ethylene oxide.

It has now been discovered that when the promoter comprises a combination of one or more first promoters selected from cesium, rubidium, and mixtures thereof and one or more second promoters selected from sodium, lithium, and mixtures thereof in specified concentrations, not only are beneficial enhancements in reaction activity and/or efficiency observed, which are typical of adding promoters to silver catalysts; but benefits are obtained when the process is challenged by a reactor upset. In fact, rather than observing a slow return to pre-upset levels of activity and/or selectivity, or not ever reaching these pre-upset levels at all, the catalyst recovers in a timely fashion, typically within about 3 days, preferably about 2 days, more preferably in about 1 day, and even more preferably in about ½ day, after restart-up to substantially pre-upset activity and/or efficiency levels. Specifically, greater than about 80 percent, and preferably, greater than about 90 percent of pre-upset activity and/or efficiency level is recovered. The meaning of the terms "pre-upset level of activity" and "pre-upset level of efficiency" have been provided hereinabove. Further, the stability of the catalyst is increased as compared to a second supported silver catalyst comprised of the same materials except that the second catalyst does not contain at least one second promoter selected from the group consisting of sodium, lithium, and mixtures thereof.

The concentration(s) of one or more first promoters (cesium, rubidium, and mixtures thereof) deposited onto the carrier may vary; but generally, the quantities are provided in a promoting amount. In this context, the term "promoting amount" means any amount of first promoter that provides an improvement in one or more of the catalytic properties of that catalyst when compared to a comparative or baseline catalyst containing the same amounts of same components, however, without the promoting component, and when compared under the same (controlled) process conditions. Examples of catalytic properties include, inter alia, resilience, operability (resistance to run-away), activity, conversion (e.g., conversion of alkene), efficiency (selectivity), stability, and yield. Preferably, the first promoter and second promoter are provided in a "synergistic combination." The term "synergistic combination" refers to quantities of first and second promoters, for example, cesium and sodium, which are capable of achieving an efficiency greater than the value obtainable under similar operating conditions from respective catalysts containing the same support, same amount of silver, and same amount(s) of other components, but which instead of containing both first promoter (e.g., cesium) and second promoter (e.g., sodium), one contains only the respective quantity of the deposited first promoter and the other contains only the respective quantity of the deposited second promoter. If lithium is also present, then a synergistic combination of first promoter and second promoters, is preferred that achieves an efficiency greater than the value obtainable under similar operating conditions from respective catalysts containing the same support, the same amount of silver, and the same amount(s) of other components, but which instead of containing first and second promoters, one contains only the respective quantity of first promoter and the second contains only the respective quantity of the second promoters. U.S. Pat. No. 4,916,243, incorporated herein by reference, teaches a silver-supported catalyst containing a synergistic combination of cesium and at least one other alkali metal selected from the group consisting of lithium, sodium, potassium and rubidium. Such patent describes an efficiency equation that may be useful in identifying a synergistic combination of the cesium and other alkali metal(s); but the efficiency equation represents only one method, not the only method, of characterizing synergistic combinations.

There is no set limit for the concentrations of cesium, rubidium or mixtures thereof deposited onto the carrier in the catalyst of this invention. The amounts may be adjusted as a function of the surface area of the carrier and other factors. The concentrations of ranges in the next two paragraphs below are provided in the context of a carrier having a surface area of about 1-1.3 $m^2/g$.

In the catalyst of this invention, the concentration of cesium deposited onto the carrier typically ranges from about 0.005 to about 0.30 weight percent, calculated on the weight of the catalyst. The concentration of the deposited cesium is less than 0.30 and more preferably, less than 0.12 weight percent, calculated on the weight of the catalyst. The most preferred cesium concentration ranges from greater than about 200 to less than about 1200 parts per million (ppm) by weight, based on the weight of the catalyst.

In the catalyst of this invention, the concentration of rubidium deposited onto the carrier typically ranges from about 0.005 to about 0.30 weight percent, calculated on the weight of the catalyst. Preferably, the concentration of the deposited rubidium is less than 0.30 and more preferably, less than 0.12 weight percent, calculated on the weight of the catalyst. The most preferred rubidium concentration ranges from greater than about 200 to less than about 1200 parts per million (ppm) by weight, based on the weight of the catalyst.

The amounts of the second promoter (sodium, lithium, or mixtures thereof) may be adjusted as a function of the surface area of the carrier and other factors. The concentrations of ranges in the following two paragraphs are provided in the context of a carrier having a surface area of about 1-1.3 $m^2/g$.

In the catalyst of the invention, the concentration of sodium deposited onto the carrier typically ranges from about 10, 20, or 30 ppm to about 250 ppm, calculated on the weight of the catalyst. The concentration of the deposited sodium is preferably greater than about 10 ppm, more preferably, greater than about 15 ppm, and most preferably, greater than about 20 ppm by weight, calculated on the weight of the catalyst. The concentration of the deposited sodium is preferably less than about 250 ppm, more preferably, less than about 200 ppm, and most preferably, less than about 150 ppm by weight, based on the weight of the catalyst.

In the catalyst of this invention, the concentration of lithium deposited onto the carrier typically ranges from about 10, 13, or 15 ppm to about 500 ppm by weight, calculated on the weight of the catalyst. The concentration of the deposited lithium is preferably greater than about 10 ppm, more preferably, greater than about 15 ppm, and most preferably, greater than about 20 ppm by weight, calculated on the weight of the catalyst. The concentration of the deposited lithium is preferably less than about 500 ppm, more preferably, less than about 250 ppm, and most preferably, less than about 100 ppm by weight, based on the weight of the catalyst.

Well known methods can be employed to analyze for the amounts of silver, first promoter, second promoter, and optional other solid promoters deposited onto the alumina carrier. The skilled artisan may employ, for example, material balances to determine the amounts of any of these deposited components. As an example, if the alumina carrier is weighed prior to and after deposition of silver and an alkali metal-containing compound, then the difference in the two weights will be equal to the amount of silver and the alkali metal-containing compound deposited onto the carrier, from which the amount of the deposited alkali metal can be calculated. Additionally, the amount of the deposited silver and alkali metal-containing compound can be calculated based upon the ratio of the concentration of silver and alkali metal-containing compounds in the impregnation solutions and the total weight in the finished catalyst picked up from the impregnation solutions. The amount of deposited silver and promoters can also be determined by leaching the catalyst with 10% nitric acid for one hour at about 90° C. and determining extracted species by standard Atomic Absorption spectroscopy techniques. Inductively Coupled Plasma Spectroscopy techniques may also be used for such determinations. Alternatively, any suitable analytical technique for determining elemental composition, such as X-ray fluorescence (XRF), may be employed to determine the amounts of the deposited components. As an example, an alumina carrier can be analyzed by XRF to determine the amount of cesium present in the carrier. After impregnation with a cesium-containing compound, the impregnated carrier may be analyzed by XRF again to determine the total amount of cesium present in and deposited onto the carrier. The difference in the measurements reflects the amount of cesium deposited onto the carrier.

Besides the first and second promoters described hereinabove, at least two other general types of promoters—solid promoters and gaseous promoters—may, if desired, be employed with the catalyst of this invention. (The term "having deposited thereon", is not meant to exclude the presence of other promoters.) A solid promoter is incorporated into the catalyst prior to its use, either as a part of the carrier (that is support) or as a part of the silver component applied thereto. When a solid promoter is added during the preparation of the catalyst, the promoter may be added to the carrier before the silver component is deposited thereon, added simultaneously with the silver component, or added sequentially following the deposition of the silver component on the carrier. Those of skill in the art are well-acquainted with such promoters. Examples of well-known solid promoters for catalysts used to produce alkylene oxides, particularly ethylene oxide, include compounds of rhenium, sulfur, manganese, molybdenum, and tungsten. As optional solid promoters, compounds of the Group 3b through Group 7b elements of the Periodic Table may be employed. Note that references to the Periodic Table herein shall be to that published by the Chemical Rubber Company, Cleveland, Ohio, in CRC Handbook of Chemistry and Physics, 46$^{th}$ Edition (inside back cover). During the reaction to make alkylene oxide, the specific form of the promoter on the catalyst may be unknown.

In contrast, the gaseous promoters are gas-phase compounds and/or mixtures thereof which are introduced to a reactor for the production of alkylene oxide (preferably, ethylene oxide) with the vapor-phase reactants, such as ethylene and oxygen. Such promoters, also called modifiers, inhibitors, or enhancers, further enhance the performance of a given catalyst, working in conjunction with or in addition to the solid promoters. One or more chlorine-containing components are typically employed as gaseous promoters, as is well known in the art. Other halide-containing components may also be used to produce a similar effect.

The first and second promoters and any optional solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counter ion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst as prepared and/or under reaction conditions.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than about 5 percent, greater than about 10 percent, greater than about 20 percent, greater than about 25 percent, preferably, greater than about 27 percent, and more preferably, greater than about 30 percent by weight, based on the weight of the catalyst. Typically, the amount of silver supported on the carrier is less than about 70 percent, preferably, less than about 50 percent, and more preferably, less than about 40 percent by weight, based on the weight of the catalyst.

The silver solution used to impregnate the carrier is preferably comprised of a silver compound in a solvent or complexing/solubilizing agent such as the silver solutions disclosed in the art. The particular silver compound employed may be chosen, for example, from among silver complexes, silver nitrate, silver oxide, or silver carboxylates, such as silver acetate, oxalate, citrate, phthalate, lactate, propionate, butyrate and higher fatty acid salts. Silver oxide complexed with amines is another preferred form of silver for use in the present invention.

A wide variety of solvents or complexing/solubilizing agents may be employed to solubilize silver to the desired concentration in the impregnating medium. Among those disclosed as being suitable for this purpose are lactic acid; ammonia; alcohols, such as ethylene glycol; and amines and aqueous mixtures of amines.

For example, silver oxide ($Ag_2O$) can be dissolved in a solution of oxalic acid and ethylenediamine to an extent of approximately 30 percent by weight. Vacuum impregnation of such a solution onto a carrier of approximately 0.7 $cm^3/g$ porosity typically results in a catalyst containing approximately 20 percent by weight of silver based on the entire weight of the catalyst. Accordingly, if it is desired to obtain a catalyst having a silver loading of greater than about 25 or 30 percent, and more, it would generally be necessary to subject the carrier to at least two or more sequential impregnations of such silver solution, with or without promoters, until the desired amount of silver is deposited on the carrier. In some instances, the concentration of the silver salt is higher in the latter impregnation solutions than in the first. In other instances, approximately equal amounts of silver are deposited during each impregnation. Often, to effect equal deposition in each impregnation, the silver concentration in the subsequent impregnation solutions may need to be greater than that in the initial impregnation solutions. In further instances, a greater amount of silver is deposited on the carrier in the initial impregnation than that deposited in subsequent impregnations. Each of the impregnations may be followed by roasting or other procedures to remove the volatile solvent and render the silver insoluble.

Although silver particle size in the finished catalyst is important, the range is not narrow. A suitable silver particle size can be in the range of from about 10 to about 10,000 angstroms in diameter. A preferred silver particle size ranges from greater than about 100 to less than about 5,000 angstroms in diameter. It is desirable that the silver, first and second promoters, and other solid promoters, if employed, be relatively uniformly dispersed within, throughout, and/or on the alumina carrier.

A preferred procedure for depositing silver catalytic material, the required first and second promoter(s) and/or one or more additional solid promoters comprises: (1) impregnating a porous alumina carrier according to the present invention with a solution comprising a solvent or solubilizing agent, silver complex and one or more of the desired promoters, and (2) thereafter treating the impregnated carrier to convert the silver salt to silver metal and effect deposition of silver and the promoter(s) onto the exterior and interior pore surfaces of the carrier. Silver and promoter depositions are generally accomplished by heating the carrier at elevated temperatures to evaporate the liquid within the carrier and effect deposition of the silver and promoters onto the interior and exterior carrier surfaces. Alternatively, a coating of silver, first promoter, second promoter and/or other solid promoters may be formed on the carrier from an emulsion or slurry containing the metal components followed by heating the carrier as described hereinabove. Impregnation of the carrier is generally the preferred technique for silver deposition, because it utilizes silver more efficiently than coating procedures, the latter being generally unable to effect substantial silver deposition onto the interior surfaces of the carrier. In addition, coated catalysts are more susceptible to silver loss by mechanical abrasion.

As with the silver deposition, soluble salts of the first and second promoters, and optional other solid promoters may be dissolved in one or more solvents and/or solubilizing agents and deposited, preferably by impregnation, onto the carrier. The sequence of impregnating or depositing the surfaces of the carrier with silver, first promoter, second promoter and optional other solid promoters may vary. Thus, impregnation and deposition of silver, first promoter, and second promoter may be effected coincidentally or sequentially, for example, cesium and sodium may be deposited prior to, during, or subsequent to silver deposition to the carrier. The first and second promoters may be deposited together or sequentially. For example, silver may be deposited first followed by the coincidental or sequential deposition of cesium and sodium; or alternatively, sodium may be deposited first followed by coincidental or sequential deposition of silver and cesium; or alternatively, cesium may be deposited first followed by coincidental or sequential deposition of silver and sodium. If two or more impregnations are employed, the impregnated carrier is typically dried, or calcined and/or roasted between each successive impregnation to ensure deposition of the metals onto the carrier.

A preferred procedure for depositing the metal components comprises a two-step impregnation. In a first step (1), the alumina carrier is impregnated with a solution comprising a solvent or solubilizing agent and a silver salt in an amount sufficient to deposit the desired weight of silver upon the carrier. Thereafter, the impregnated carrier is calcined under air (or other atmospheres, such as in nitrogen, helium, and/or steam) at a temperature ranging from about 200° C. to about 600° C. and at atmospheric pressure for a time ranging from about 0.01 to about 12 hours. Prior to the calcination, optionally, the impregnated carrier may be dried in an oven to remove the solvent. In a second step (2), the silver-impregnated carrier is impregnated with a solution containing additional silver compound and promoting amounts of soluble salts of first promoter, second promoter, and optional, other solid promoters. Preferably, a synergistic combination of first promoter and second promoters is employed. Thereafter, the carrier now impregnated with silver, and first and second promoters, is calcined or roasted under air at a temperature ranging from about 200° C. to about 600° C. and at atmospheric pressure for a time ranging from about 0.01 to about 12 hours.

Aside from the required first and second promoters, which have already been discussed, the preferred amount of optional cationic solid promoter deposited on the carrier or present in the catalyst generally lies between about 10 and about 4,000, preferably, between about 15 and about 3,000, and more preferably, between about 20 and about 2,500 ppm by weight cation, calculated on the weight of the catalyst. Amounts between about 20 and about 2,500 ppm by weight of cation are frequently most preferred.

Examples of some anion promoters that may be employed with the present invention include the halides, for example, fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten, and rhenium may be preferred for some applications. By way of non-limiting example, the types of anion promoters suitable for use in the catalyst of this invention comprise oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $Moa_4^{-2}$, vanadates, for example, $V_2O_4^{-2}$, chromates, for example, $CrO_4^{-2}$, zirconates, for example, $ZrO_3^{-}$2, polyphosphates, manganates, nitrates, chlorates, bromates, borates, silicates, carbonates, tungstates, thiosulfates, cerates, and mixtures thereof. The halides may also be present, including fluoride, chloride, bromide, iodide, and mixtures thereof. A preferred anion promoter is sulfate ($SO_4^{-2}$).

Solely for the purposes of calculating the following ratios, we assume that, where present, the sulfur compound promoter is present on the catalyst as a divalent sulfate species, the molybdenum promoter is present on the catalyst as a divalent molybdate species, the tungsten promoter is present on the catalyst as a divalent tungstate species, and the rhenium promoter is present on the catalyst as a monovalent perrhenate species.

When the catalyst does not contain a rhenium promoter, the ratio is calculated as (charge number of anion)×(moles of anion) divided by total moles of cesium and sodium, if present e.g., [(2S)/(Cs+Na)], ranges from about 0.5/1 to about 1.5/1, but a preferred range is from about 0.7/1 to about 1.5/1.

When the catalyst contains a rhenium promoter, the ratio ranges from 0.5 to 1.5, more preferably 0.6 to 1.2, and even more preferably 0.7 to 1.1. The ratio is calculated as 2(moles sulfur plus moles tungsten plus moles molybdenum) plus moles Re divided by the total moles of cesium and sodium, if present, i.e., [(2(S+W+Mo)+Re)/(Cs+Na)].

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$, and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental, or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

When the promoter comprises rhenium, the rhenium component can be provided in various forms, for example, as the metal, as a covalent compound, as a cation, or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides, and the acids of rhenium. However, the alkali metal perrhenates, ammonium perrhenate, alkaline earth metal perrhenates, silver perrhenates, other perrhenates, and rhenium heptoxide can also be suitably utilized, provided that in the case of the alkali metal perrhenates, the quantities of alkali metals (Cs and/or Rb; and Na and/or K and/or Li) therein are taken into account when assessing the total of these cations deposited onto the carrier. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten. When rhenium is a promoter, other promoters, such as compounds of sulfur, molybdenum, tungsten, and mixtures thereof are often used. These compounds are sometimes referred to as "rhenium co-promoters".

Another class of preferred promoters and catalyst stabilizers, which may be employed with the present invention, includes manganese components. In many instances, manganese components can enhance the activity, efficiency, and/or stability of catalysts. The manganese species that provides the enhanced activity, efficiency, and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and mixtures thereof. To stabilize the manganese component in certain impregnating solutions, it may be necessary to add a chelating compound, such as, ethylenediaminetetraacetic acid (EDTA) or a suitable salt thereof.

The amount of anion promoter may vary widely, for example, from about 0.0005 to not greater than about 2 weight percent, preferably from about 0.001 to about 0.5 weight percent, calculated as the weight of the metal in the promoter and based on the weight of the catalyst. When the carrier surface area is in the range of 1-1.3 m²/g, when used, the rhenium component is often provided in an amount of at least about 5 ppm, preferably, at least about 10 ppm, for example, from about 10 ppm to about 2000 ppm, and more preferably, between about 20 ppm and about 1000 ppm by weight, calculated as the weight of rhenium and based on the weight of the catalyst. When the carrier surface area is in the range of 1-1.3 m2/g, when used, the manganese component is often provided in an amount of at least about 5 ppm, preferably, at least about 10 ppm, for example, from about 10 ppm to about 1000 ppm, and more preferably, between about 20 ppm and about 300 ppm by weight, calculated as the weight of manganese and based on the weight of the catalyst.

In one embodiment, the amount of manganese added is at least about 1.5 micromoles per gram of catalyst.

The promoting effect(s) provided by the first and second promoters, and optional other cation and anion promoters and/or solid and gas phase promoters can be affected by a number of variables, for example, reaction conditions, catalyst preparation techniques, surface area and pore structure, and surface chemical properties of the support, the silver, and the concentrations of the promoters present in the catalyst.

The present invention is applicable to epoxidation reactions in any suitable reactor, for example, fixed bed reactors, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas to a catalyst-containing reactor at a temperature of from about 200° C. to about 300° C., and a pressure which may vary within the range of from about 5 atmospheres (506 kPa) to about 30 atmospheres (3.0 MPa), depending upon the mass velocity and productivity desired. Residence times in large-scale reactors are generally on the order of about 0.1 to about 5 seconds. Oxygen may be supplied to the reaction in an oxygen-containing stream, such as, air or as commercial oxygen, or as oxygen-enriched air. The resulting alkylene oxide, preferably, ethylene oxide, is separated and recovered from the reaction products using conventional methods.

The alkylene oxide produced using the catalyst of the present invention or by the method of the present invention may be converted into alkylene glycols, alkanolamines and glycol ethers. Ethylene glycol is used in two significant applications: as a raw material for poly(ethylene terephthalate) for use in polyester fiber, film, and containers, and as an automotive antifreeze. Di-, tri-, and tetraethylene glycols are coproducts of ethylene glycol. Ethylene glycol can be produced by the (catalyzed or uncatalyzed) hydrolysis of ethylene oxide. Ethylene oxide hydrolysis proceeds with either acid or base catalysis or uncatalyzed in neutral medium. Acid-catalyzed hydrolysis activates the ethylene oxide by protonation for the reaction with water. Base-catalyzed hydrolysis results in considerably lower selectivity to ethylene glycol. A principal by-product is diethylene glycol and higher glycols, triethylene and tetraethylene glycols, are also produced. Ethylene glycol monoethers can be manufactured by reaction of an alcohol with ethylene oxide. Ethanolamine can be manufactured by the reaction of ethylene oxide with ammonia. See, e.g., U.S. Pat. No. 4,845,296, which is incorporated herein by reference.

The catalysts disclosed herein can be used under widely varying process conditions, as is well known by those skilled in the art. However, for purposes of defining standard sets of conditions under which the activity, efficiency, stability, resiliency, and other factors obtained using a particular catalyst can be compared, a standard set of process conditions referred to herein as "Standard Ethylene Epoxidation Process Conditions" may be useful. These standard conditions are described for illustrative purposes only and should not limit the invention in any manner. Other standardized conditions and reaction process conditions may be equally suitable.

Standard Ethylene Epoxidation Process Conditions ("Conditions")

A standard back-mixed autoclave with gas recycle is used for catalyst testing, or alternatively a tubular reactor. Some variation in gas phase feed concentrations may occur depending upon the process conditions used in the test or in a commercial plant. Well known, back-mixed, bottom-agitated "Magnedrive" autoclaves described in FIG. 2 of the paper by J. M. Berty entitled "Reactor for Vapor Phase- Catalytic Studies," in Chemical Engineering Progress, Vol. 70, No. 5, pages 78-84, 1974, may be used.

Two cases of CONDITIONS are described: one for air process conditions, which simulate typical conditions employed in commercial air-type ethylene oxide processes where air is used to supply molecular oxygen; and one for oxygen process conditions, which simulate typical conditions in commercial oxygen-type ethylene oxide processes where pure oxygen is added as the oxygen source. Each case may provide a different efficiency for like catalysts; but it is the rule for practically all cases that with air as the oxygen feed, lower concentrations of oxygen and ethylene are used that yield an efficiency to ethylene oxide which is about 2 to 5 percentage points lower than that when pure oxygen is employed as oxygen source. The CONDITIONS employ 2.0 mole % ethylene oxide in the outlet gas of the reactor when the inlet conditions include the following:

Ethylene Epoxidation Inlet Process Conditions

| Component | Air Process Conditions Mole % | Oxygen Process Conditions Mole % |
|---|---|---|
| Ethylene | 11.0 | 30.0 |
| Oxygen | 7.0 | 8.0 |
| Ethane | 0.00-0.24 | 0.5 |
| Carbon Dioxide | 5.5 | 6.5 |
| Nitrogen | Balance of gas | Balance of gas |
| Parts per million Ethyl Chloride | Optimum for Efficiency | Optimum for Efficiency |
| Type of Reactor | CSTR[a] | CSTR[a] |
| Amount of Catalyst[c] | 80 cm$^3$ | 80 cm$^3$ |
| Total Inlet Flow Rate[b] | 22.6 SCFH[d] | 22.6 SCFH[d] |

[a]CSTR = continuous stirred tank reactor
[b]Mass flow rate is calibrated on nitrogen gas.
[c]40 cm$^3$ are used for a Rotoberty test
[d]SCFH = cubic feet per hour at standard conditions (0° C. and 1 atmosphere)

The pressure is maintained at about 275 psig (pounds per square inch, gauge) (2000 kPa) and the total flow is maintained at about 11.3 or 22.6 SCFH (Standard Cubic Feet per Hour). SCFH refers to cubic feet per hour at standard temperature and pressure, namely, 0° C. and one atmosphere. The flow rate is calibrated with a nitrogen stream. Except as otherwise specified, ethyl chloride concentration is adjusted to achieve maximum efficiency. Temperature (° C.) and catalyst efficiency are obtained as the responses describing the catalyst performance.

The catalyst test procedure used for autoclaves in the Standard Ethylene Epoxidation Process Conditions involves the following: 40 or 80 cm$^3$ of catalyst is charged to the back-mixed autoclave and the weight of the catalyst is noted. The back-mixed autoclave is heated to about reaction temperature in a nitrogen flow of 10 or 20 SCFH with the fan operating at 1500 rpm. The nitrogen flow is then discontinued and the above-described feed stream is introduced into the reactor. The total gas inlet flow is then adjusted to 11.3 SCFH for 40 cm$^3$ of catalyst or 22.6 SCFH for 80 cm$^3$ of catalyst. The temperature is adjusted over the next few hours to provide the desired percent outlet ethylene oxide and the optimum efficiency is obtained by adjusting ethyl chloride, a chlorine-containing reaction modifier species. In one type of test, the outlet ethylene oxide concentration is monitored to make certain that the catalyst has reached its peak performance. As the catalyst ages, the temperature is periodically adjusted (e.g., increased) to maintain constant ethylene oxide production. The rate of deactivation (temperature rise) and efficiency decline at constant ethylene oxide production at outlet are thus measured and obtained. In a different type of test, the temperature may be fixed and the outlet ethylene oxide concentration and efficiency may be monitored as the catalyst ages.

The standard deviation of a single test result reporting catalyst efficiency in accordance with the procedures described herein is about 0.3 percent efficiency units. The typical standard deviation of a single test result reporting catalyst activity in accordance with the procedure described above is about 1.2° C. The standard deviation, of course, will depend upon the quality of the equipment and precision of the techniques used in conducting the tests, and thus will vary. These standard deviations are believed to apply to the test results reported herein.

In another set of process conditions that is suitable for evaluating the catalysts of this invention, a fixed-bed tubular (plug-flow) reactor is employed at the operating conditions of 4700 gas hourly space velocity, a pressure of 21.7 barg, and a work rate of 184 kg per m$^3$ per hour with a reactor feed containing 25 mole % ethylene, 8 mole % oxygen, 2 mole % carbon dioxide, and one or more chlorine-containing reaction modifier species, the concentration of which is adjusted such that the selectivity towards ethylene oxide formation is optimal. Test results may be obtained with the reactor configured for single-pass operation or with a portion of the reactor outlet stream recycled back to form part of the reactor inlet feed following removal of ethylene oxide and, optionally, at least a portion of the carbon dioxide in one or more absorption units.

The catalyst of this invention provides for acceptable levels of activity and/or alkylene oxide efficiency, and preferably also, stability, before and after a reactor upset. A preferred (not necessarily the least acceptable level) of activity for catalysts not comprising a rhenium promoter, is measured typically as greater than about 1.0 mole percent, and preferably, greater than about 1.5 mole percent alkylene oxide in the outlet stream; or for a fresh catalyst, at a temperature less than about 230° C. to maintain an outlet alkylene oxide concentration greater than about 1.5 percent. A preferred (not necessarily the least acceptable level) of efficiency for catalysts not comprising a rhenium promoter is typically greater than about 70, preferably, greater than about 75, and more preferably, greater than about 80 percent selectivity to alkylene oxide. In preferred embodiments of this invention, an efficiency to alkylene oxide of greater than about 75 percent is achieved at high workrates, namely, a workrate greater than about 4, and preferably, greater than about 5, and more preferably, equal to or greater than about 6 kg-mol AO/h/m$^3$.

A preferred (not necessarily the least acceptable level) of activity for catalysts comprising a rhenium promoter, is measured typically as greater than about 1.0 mole percent, and preferably, greater than about 1.5 mole percent alkylene oxide in the outlet stream; or for a fresh catalyst, at a temperature less than about 240° C. to maintain an outlet alkylene oxide concentration greater than about 1.5 percent. A preferred (not necessarily the least acceptable level) of efficiency for catalysts comprising a rhenium promoter is typically greater than about 80, preferably, greater than about 85 percent selectivity to alkylene oxide. In preferred embodiments of this invention, an efficiency to alkylene oxide of greater than about 80 percent is achieved at high workrates, namely, a workrate greater than about 3, and preferably, greater than about 4, and more preferably, equal to or greater than about 5 kg-mol AO/h/m$^3$ of catalyst.

In preferred embodiments, the preferred alkylene oxide is ethylene oxide. The catalyst of this invention provides for greater than about 80 percent, and preferably, greater than about 90 percent recovery to pre-upset levels of catalyst activity and/or efficiency within about 3 days, preferably about 2 days, more preferably in about 1 day, and ever more preferably in about ½ day, following re-startup from a reactor upset. The catalyst exhibits increased stability as compared to a second supported silver catalyst comprised of the same materials except that the second catalyst does not contain at least one second promoter selected from the group consisting of sodium, lithium, and mixtures thereof.

The following examples are set forth for the purpose of illustrating the invention; but these examples are not intended to limit the invention in any manner. One skilled in the art will recognize a variety of substitutions and modifications of the examples that will fall within the scope of the invention.

Carrier Preparation

An alpha-alumina carrier comprising platelet morphology and greater than about 96 weight percent alpha-alumina and about 2 weight % zirconium silicate is used. Using the nitric acid leachable methodology, Carrier A has 0.04 ppm Li, and about 7.1 ppm Na and less than 0.9 ppm K, Carrier B has 0.05 ppm Li, less than 0.9 ppm K and about 5 ppm Na. Carrier C has between about 2.9 to 3.4 ppm Na, less than 0.03 Li, and less than 2 ppm K. The surface area of the carrier is measured by nitrogen BET, and the pore volume and median pore diameter are measured by mercury porosimetry. Carriers having these properties can be made pursuant to procedures described in WO-A1-2005/039757, such as those for Carriers C-D, and F-M therein. (Carrier E, if containing less than 30 ppm acid leachable sodium, potassium, and lithium by weight, calculated on the weight of the carrier, would also be acceptable.)

Nitric acid leachable methodology: the samples are prepared in duplicate by leaching 2 grams of unground carrier in ~22 grams 10% nitric acid solution (prepared by adding 10 mL concentrated nitric acid to 90 mL ASTM type 1 water). The samples are heated in a constant temperature oven for one hour at 90° C. The samples are cooled to room temperature and filtered with a 0.45% micron syringe filter. Each solution is analyzed on a Perkin-Elmer Optima 3300 RL Inductively Coupled Plasma ("ICP") emission spectrometer. The average of five consecutive analyses is reported; the Relative Standard Deviation of the average was typically <5%.

TABLE II

Carrier Properties

| Carrier ID | A | B | C |
|---|---|---|---|
| Surface Area (m$^2$/g) | 1.19 | 1.12 | 0.85 |
| Packing Density *(lb/ft$^3$) | 31.7 | 31.8 | 33.0 |
| Median Pore Diameter (μm) | 2.1 | 2.5 | 2.6 |
| Pore Volume (cc/g) | 0.73 | 0.70 | 0.64 |

* The packing density is measured by ASTM D4699-03, "Standard Test Method for Vibratory Packing Density of Large Formed Catalyst and Catalyst Particles", modified by the use of a cylinder with an inside diameter of 3¾ inches and a length of 18 inches, or the equivalent.

Catalyst Preparation

The carriers are vacuum impregnated with a first impregnation silver solution typically containing 30 weight percent silver oxide, 18 weight percent oxalic acid, 17 weight percent ethylenediamine, 6 weight percent monoethanolamine, and 27 weight percent distilled water. The first impregnation solution is typically prepared by (1) mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The carrier is impregnated in an appropriately sized glass or stainless steel cylindrical vessel which is equipped with suitable stopcocks for impregnating the carrier under vacuum. A suitable separatory funnel which is used for containing the impregnating solution is inserted through a rubber stopper into the top of the impregnating vessel. The impregnating vessel containing the carrier is evacuated to approximately 1-2" mercury absolute for 10 to 30 minutes, after which the impregnating solution is slowly added to the carrier by opening the stopcock between the separatory funnel and the impregnating vessel. After all the solution empties into the impregnating vessel (~15 seconds), the vacuum is released and the pressure returned to atmospheric. Following addition of the solution, the carrier remains immersed in the impregnating solution at ambient conditions for 5 to 30 minutes, and is thereafter drained of excess solution for 10 to 30 minutes.

The silver-impregnated carrier is then roasted as follows to effect reduction of silver on the catalyst surface. The impregnated carrier is spread out in a single layer on stainless steel wire mesh trays then placed on a stainless steel belt (spiral weave) and transported through a 2"×2" square heating zone for 2.5 minutes, or equivalent conditions are used for a larger belt operation. The heating zone is maintained at 500° C. by passing hot air upward through the belt and the catalyst particles at the rate of 266 standard cubic feet per hour (SCFH). After being roasted in the heating zone, the catalyst is cooled in the open air to room temperature and weighed.

Next, the silver-impregnated carrier is vacuum impregnated with a second silver impregnation solution containing both the silver oxalate amine solution and the catalyst promoters. The second impregnation solution is composed of all of the drained solution from the first impregnation plus a fresh aliquot of the first solution, or a new solution is used. The promoters, added with stirring in order to solubilize them, are added with the goal of achieving the desired target levels on the finished catalysts. Table III and Table IV shows the amounts of the promoters and stabilizing agent (diammonium EDTA) added to each catalyst in the second impregnation. The impregnation, draining and roasting steps for this second impregnation are carried out analogously to the first impregnation. The twice-impregnated carrier, that is the finished catalyst, is again weighed. Based upon the weight gain of the carrier in the second impregnation, the weight percent of silver is calculated. The concentration of the promoters are calculated, assuming a similar rate of deposition for the promoters as for the silver (results given in Table III and Table IV, except that the amounts for Comparative Catalyst 6 are the target amounts as opposed to calculated amounts). In some cases, the preparation of a catalyst is carried out on a larger or smaller scale than that described here using suitable scale-up or scale-down of equipment and methods.

The finished catalyst is then employed in an ethylene epoxidation reaction, the results of which are given in the Examples. The properties of the as-prepared catalysts are shown in Table III or Table IV.

TABLE III

| Catalyst Preparations | | | | | |
|---|---|---|---|---|---|
| Catalyst No. | 1 | 2 | 3 | 4 | 5 Comparative |
| First Impregnation | | | | | |
| Carrier ID | A | A | A | A | B |
| Carrier, g. | 1775.39 | 2700 | 225.2 | 62.55 | 50.43 |
| Silver oxalate amine solution, g. | 5911.2 | 6715 | 661.1 | 223.5 | 221.55 |
| Weight Ag in soln., % | 26.94 | 27.4 | 27.5 | 26.06 | 26.58 |
| Soln. density, g/cc | 1.48 | 1.49 | 1.47 | 1.49 | 1.477 |
| 1st Silver loading, g. | 516.61 | 815 | 68.0 | 19.10 | 15.19 |
| Silver loading, % | 22.54 | 23.2 | 23.2 | 23.4 | 23.15 |
| Second Impregnation | | | | | |
| First dip catalyst, g. | 2292.0 | 3515 | 25.15 | 81.65 | 65.62 |
| Silver oxalate amine solution, g. | 5905.6 | 6723.1 | 110.2 | 223.50 | 221.55 |
| Weight Ag in soln., % | 26.94 | 27.4 | 27.5 | 26.06 | 26.58 |
| Soln. density, g/cc | 1.48 | 1.49 | 1.45 | 1.49 | 1.477 |
| Promoter soln. A | $Mn(NO_3)_2$ 0.1615 g Mn/g | $Mn(NO_3)_2$ 0.162 g Mn/g | $Mn(NO_3)_2$ 0.165 g Mn/g | $Mn(NO_3)_2$ 0.1565 g Mn/g | $Mn(NO_3)_2$ 0.157 g Mn/g |
| Promoter soln. A, g. | 4.515 | 5.47 | 0.084 | 0.2260 | 0.2084 |
| Promoter soln. B | $Li_2(O_2C_2H_3)$ 0.0667 g Li/g | $(NH_4)_2SO_4$ 0.727 g SO4/g | $(NH_4)_2SO_4$ 0.727 g SO4/g | $(NH_4)_2SO_4$ 0.2016 g SO4/g | $Cs_2SO_4$ 0.420 g SO4/g |
| Promoter soln. B, g. | 4.101 | 4.66 | 0.144 | 0.2110 | 0.3150 |
| Promoter soln. C | CsOH 0.459 g Cs/g | CsOH 0.459 g Cs/g | CsOH 0.455 g Cs/g | CsOH 0.4530 g Cs/g | CsOH 0.4530 g Cs/g |
| Promoter soln. C, g. | 7.941 | 9.89 | 0.44 | 0.3781 | 0.0697 |
| Promoter soln. D | NaOH 0.0228 g Na/g | NaOH 0.023 | $Li_2(O_2C_2H_3)$ 0.067 g Li/g | $Li_2(O_2C_2H_3)$ 0.0273 g Li/g | $Rb_2(SO_4)$ 0.640 g Rb/g |
| Promoter soln. D, g. | 14.986 | 49.19 | 0.13 | 0.3308 | 0.1642 |
| Promoter soln. E | $(NH_4)_2SO_4$ 0.727 g SO4/g | | | $Na_2(O_2C_2H_3)$ 0.0750 g Li/g | |
| Promoter soln. E, g. | 2.829 | | | 0.1455 | |
| Promoter soln. F | | | | $NH_4ReO_4$ 0.0370 g Re/g | |
| Promoter soln. F, g. | | | | 3.2437 | |
| Chelating agent. | $(NH_4)_2$EDTA 0.453 g EDTA/g | $(NH_4)_2$EDTA 0.451 g EDTA/g | $(NH_4)_2$EDTA 0.451 g EDTA/g | $(NH_4)_2$EDTA 0.4490 g EDTA/g | $(NH_4)_2$EDTA 0.4490 g EDTA/g |
| Chelating agent., g. | 16.959 | 20.58 | 0.32 | 0.8287 | 0.7614 |
| 2nd Silver loading,, g. | 469.24 | 766.0 | 5.4 | 16.6 | 13.73 |
| Total Ag loading, % | 35.67 | 36.8 | 36.6 | 36.29 | 36.26 |
| Promoter A, ppm | Mn, 78 | Mn, 85 | Mn, 79 | Mn, 103 | Mn, 95 |
| Promoter B, ppm | Li, 29 | SO4, 327 | SO4, 604 | SO4, 124 | SO4, 311 |
| Promoter C, ppm | Cs, 389 | Cs, 438 | Cs, 1162 | Cs, 498 | Cs, 476 |
| Promoter D, ppm | Na, 36 | Na, 108 | Li, 48 | Li, 26 | Rb, 306 |
| Promoter E, ppm | SO4, 219 | | | Na, 32 | |
| Promoter F, ppm | | | | Re, 349 | |

TABLE IV

| Catalyst Preparations | | | | |
|---|---|---|---|---|
| Catalyst No. | 6 Comparative | 7 Comparative | 8 | 9 |
| First Impregnation | | | | |
| Carrier ID | C | A | A | A |
| Carrier, g. | | 42.47 | 62.53 | 61.52 |
| Silver oxalate amine solution, g. | | | | |
| Weight Ag in soln., % | | 26.06 | 26.06 | 26.06 |
| Soln. density, g/cc | | | | |
| 1st Silver loading, g. | | 12.55 | 18.22 | 17.59 |
| Silver loading, % | | 22.8 | 22.6 | 22.2 |
| Second Impregnation | | | | |
| First dip catalyst, g. | | 55.02 | 80.75 | 79.11 |
| Silver oxalate amine solution, g. | | 149.0 | 223.5 | 223.5 |
| Weight Ag in soln., % | | 26.06 | 26.06 | 26.06 |
| Soln. density, g/cc | | 1.49 | 1.49 | 1.49 |
| Promoter soln. A | $Mn(NO_3)_2$ | $Mn(NO_3)_2$ 0.1565 g Mn/g | $Mn(NO_3)_2$ 0.1565 g Mn/g | $Mn(NO_3)_2$ 0.1565 g Mn/g |
| Promoter soln. A, g. | | 0.1688 | 0.2340 | 0.2369 |

TABLE IV-continued

| Catalyst Preparations | | | | | |
|---|---|---|---|---|---|
| Promoter soln. B | Cs2SO4 | (NH4)2SO4 0.2016 g SO4/g | (NH4)2SO4 0.2016 g SO4/g | (NH4)2SO4 0.2016 g SO4/g | |
| Promoter soln. B, g. | 0.1466 | 0.5304 | 0.3393 | | |
| Promoter soln. C | CsOH | NH4ReO4 0.0370 g Re/g | NH4ReO4 0.0370 g Re/g | NH4ReO4 0.0400 g Re/g | |
| Promoter soln. C, g. | 2.0794 | 3.3444 | 3.1284 | | |
| Promoter soln. D | | CsOH 0.4530 g Cs/g | Na(OCOCH3) 0.0750 g Na/g | Na(OCOCH3) 0.0750 g Na/g | |
| Promoter soln. D, g. | | 0.3504 | 0.1497 | 0.3088 | |
| Promoter soln. E | | | Li(OCOCH3) 0.0273 g Li/g | Li(OCOCH3) 0.0273 g Li/g | |
| Promoter soln. E, g. | | | 0.3407 | 0.6910 | |
| Promoter soln. F | | | CsOH 0.4530 g Cs/g | CsOH 0.4530 g Cs/g | |
| Promoter soln. F, g. | | | 0.7760 g | 0.3943 g | |
| Chelating agent. | (NH4)2EDTA | (NH4)2EDTA 0.4490 g EDTA/g | (NH4)2EDTA 0.4490 g EDTA/g | (NH4)2EDTA 0.4490 g EDTA/g | |
| Chelating agent., g. | | 0.6167 | 0.8555 | 0.8644 | |
| 2nd Silver loading,, g. | | 11.49 | 16.68 | 16.25 | |
| Total Ag loading, % | | 36.1 | 35.8 | 35.4 | |
| Promoter A, ppm | Mn, 85 | Mn, 118 | Mn, 108 | Mn, 109 | |
| Promoter B, ppm | SO4, 132 | SO4, 131 | SO4, 315 | SO4, 200 | |
| Promoter C, ppm | Cs, 468 | Re, 343 | Re, 364 | Re, 367 | |
| Promoter D, ppm | | Cs, 707 | Na, 33 | Na, 68, | |
| Promoter E, ppm | | | Li, 27 | Li, 55 | |
| Promoter F, ppm | | | Cs, 1034 | Cs, 523 | |

| Catalyst No. | 10 | 11 | 12 | 13 | 14 |
|---|---|---|---|---|---|
| First Impregnation | | | | | |
| Carrier ID | B | B | B | B | A |
| Carrier, g. | 1800.2 | 64.50 | 65.17 | 65.51 | |
| Silver oxalate amine solution, g. | | | | | |
| Weight Ag in soln., % | 26.51 | 26.51 | 26.51 | 26.51 | |
| Soln. density, g/cc | | | | | |
| 1st Silver loading, g. | 544.8 | 19.91 | 20.17 | 20.01 | |
| Silver loading, % | 23.2 | 23.6 | 23.6 | 23.4 | |
| Second Impregnation | | | | | |
| First dip catalyst, g. | 2345.0 | 84.41 | 85.34 | 85.52 | |
| Silver oxalate amine solution, g. | 5183 | 296.0 | 296.6 | 294.0 | |
| Weight Ag in soln., % | 26.51 | 26.51 | 26.51 | 26.51 | |
| Soln. density, g/cc | 1.48 | 1.48 | 1.48 | 1.47 | |
| Promoter soln. A | Mn(NO3)2 0.1565 g Mn/g | Mn(NO3)2 0.1565 g Mn/g | Mn(NO3)2 0.1565 g Mn/g | Mn(NO3)2 0.1565 g Mn/g | |
| Promoter soln. A, g. | 4.100 | 0.3722 | 0.3719 | 0.3712 | |
| Promoter soln. B | (NH4)2SO4 0.2016 g SO4/g | (NH4)2SO4 0.2016 g SO4/g | (NH4)2SO4 0.2016 g SO4/g | (NH4)2SO4 0.2016 g SO4/g | |
| Promoter soln. B, g. | 6.122 | 0.3451 | 0.5892 | 0.6818 | |
| Promoter soln. C | NH4ReO4 0.0396 g Re/g | NH4ReO4 0.0390 g Re/g | NH4ReO4 0.0396 g Re/g | NH4ReO4 0.0396 g Re/g | |
| Promoter soln. C, g. | 88.16 | 5.0517 | 4.9831 | 4.9751 | |
| Promoter soln. D | Na(OCOCH3) 0.0699 g Na/g | Na(OCOCH3) 0.0699 g Na/g | Na(OCOCH3) 0.0699 g Na/g | Na(OCOCH3) 0.0699 g Na/g | |
| Promoter soln. D, g. | 4.580 | 0.2594 | 0.5226 | 0.7250 | |
| Promoter soln. E | Li(OCOCH3) 0.0215 g Li/g | Li(OCOCH3) 0.0215 g Li/g | Li(OCOCH3) 0.0215 g Li/g | Li(OCOCH3) 0.0215 g Li/g | |
| Promoter soln. E, g. | 11.99 | 1.7080 | 1.3687 | 0.6766 | |
| Promoter soln. F | CsOH 0.4530 g Cs/g | CsOH 0.4530 g Cs/g | CsOH 0.4530 g Cs/g | CsOH 0.4530 g Cs/g | |
| Promoter soln. F, g. | 11.00 | 0.6210 | 0.6859 | 0.6210 | |
| Chelating agent. | (NH4)2EDTA 0.4490 g EDTA/g | (NH4)2EDTA 0.4490 g EDTA/g | (NH4)2EDTA 0.4490 g EDTA/g | (NH4)2EDTA 0.4490 g EDTA/g | |
| Chelating agent., g. | 14.96 | 1.3628 | 1.3620 | 1.3629 | |
| 2na Silver loading,, g. | 481.7 | 18.04 | 18.16 | 17.88 | |
| Total Ag loading, % | 36.3 | 37.0 | 37.0 | 36.6 | 36.47 |
| Promoter A, ppm | Mn, 80 | Mn, 131 | Mn, 130 | Mn, 129 | Mn, 109 |
| Promoter B, ppm | SO4, 153 | SO4, 156 | SO4, 264 | SO4, 304 | SO4, 131 |
| Promoter C, ppm | Re, 433 | Re, 441 | Re, 439 | Re, 436 | Re, 368 |
| Promoter D, ppm | Na, 40 | Na, 41 | Na, 81 | Na, 112 | Na, 34 |
| Promoter E, ppm | Li, 32 | Li, 82 | Li, 66 | Li, 32 | Li, 28 |
| Promoter F, ppm | Cs, 617 | Cs, 630 | Cs, 692 | Cs, 623 | Cs, 526 |

Example 1

A sample of Catalyst 1 (40 cm³) is evaluated in a continuously-stirred tank reactor in the epoxidation of ethylene with oxygen under the following process conditions: inlet gas in mole percent: approximately 0.5 percent ethane, 4 ppm (molar) ethyl chloride, and variable concentrations of ethylene, oxygen, and $CO_2$ in nitrogen as required to maintain constant concentrations of the same components in the effluent stream, as noted hereinafter;

total inlet flow, 0.27 m³/h (9.3 SCFH for GHSV of 6,680/h)

total inlet pressure, 2000 kPa (absolute, or 275 psig)

temperature, 225-240° C.

The composition of ethylene, oxygen, and $CO_2$ in the inlet gas is varied with time so that the outlet effluent comprises 27.0 percent ethylene, 6.0 percent oxygen, 3.0 percent carbon dioxide, 2.5 percent ethylene oxide (equivalent to a workrate of 7.5 kg-mol EO/h/m³), and a balance of nitrogen. The efficiency (EO selectivity) of the catalyst as a function of cumulative ethylene oxide production, in thousand kg EO per cubic meter of reactor volume, is shown in FIG. 1. Each data point in FIG. 1 represents a daily (24 h) average of catalyst efficiency. Table V provides the data plotted in FIG. 1 as well as the time on stream in days of operation (not necessarily consecutive calendar days). The stability of the catalyst is increased as compared to a second supported silver catalyst comprised of the same materials except that the second catalyst does not contain at least one second promoter selected from the group consisting of sodium, lithium, and mixtures thereof.

TABLE V

Data Plotted in FIG. 1

| Time On Stream [Days of Operation] | Cumulative EO Production [thousand kg/m³] | Selectivity [%] |
| --- | --- | --- |
| 3 | 17 | 79.7 |
| 4 | 25 | 80.0 |
| 5 | 33 | 80.0 |
| 6 | 41 | 80.8 |
| 7 | 49 | 81.0 |
| 8 | 57 | 80.9 |
| 9 | 64 | 80.6 |
| 10 | 72 | 80.7 |
| 11 | 80 | 80.8 |
| 12 | 88 | 80.8 |
| 13 | 96 | 80.9 |
| 14 | 103 | 81.0 |
| 15 | 111 | 81.0 |
| 16 | 119 | 81.3 |
| 17 | 127 | 80.9 |
| 18 | 135 | 80.9 |
| 19 | 142 | 80.9 |
| 20 | 150 | 81.1 |
| 21 | 158 | 81.0 |
| 22 | 166 | 80.9 |
| 23 | 173 | 81.1 |
| 24 | 181 | 81.2 |
| 25 | 189 | 81.1 |
| 26 | 197 | 81.1 |
| 27 | 205 | 81.0 |
| 28 | 213 | 81.0 |
| 29 | 221 | 81.0 |
| 30 | 228 | 81.0 |
| 31 | 236 | 80.9 |
| 32 | 244 | 80.7 |
| 33 | 252 | 80.7 |
| 34 | 260 | 80.8 |
| 35 | 268 | 80.6 |
| 36 | 276 | 80.6 |
| 37 | 284 | 80.5 |
| 38 | 292 | 80.6 |
| 39 | 300 | 80.5 |
| 40 | 307 | 80.4 |
| 41 | 315 | 80.3 |
| 42 | 323 | 80.3 |
| 43 | 331 | 80.2 |
| 44 | 339 | 80.3 |
| 45 | 347 | 80.1 |
| 46 | 355 | 79.9 |
| 47 | 363 | 80.0 |
| 48 | 371 | 80.0 |
| 49 | 378 | 79.7 |
| 50 | 386 | 79.6 |
| 51 | 394 | 79.7 |
| 52 | 402 | 79.9 |
| 53 | 410 | 79.6 |
| 54 | 418 | 79.5 |

Example 2

A sample of Catalyst 2 (3.65 kg) is loaded into a fixed-bed reactor and evaluated in the epoxidation of ethylene with oxygen under the following process conditions:

inlet gas in mole percent: 30 percent ethylene, 8.5 percent oxygen, 6.0 percent carbon dioxide, 0.6 percent ethane, 6.5 ppm (molar) ethyl chloride, and balance nitrogen;

total inlet flow, 20 m³/h (690 SCFH for GHSV of 3,550/h)

total inlet pressure, 2,170 kPa (absolute, or 300 psig)

temperature, 215-240° C.

The outlet effluent comprises 2.5 percent ethylene oxide (equivalent to a workrate of 4 kg-mol EO/h/m³). The ethylene oxide efficiency (EO selectivity) of the catalyst is tabulated in Table 2 as a function of cumulative EO production, in thousand kg EO produced per cubic meter of reactor volume, and the time on stream (in days of operation, not necessarily consecutive calendar days). For ease of viewing, the tabulated data are plotted in FIG. 2. Each data point in Table 2 and FIG. 2 represents a daily (24 h) average of catalyst efficiency. The resiliency of the catalyst is illustrated following several reactor upsets occurring between 400 and 600 thousand kg cumulative ethylene oxide production per cubic meter reactor volume. From both Table VI and FIG. 2, it is seen that the catalyst recovers to a pre-upset level of efficiency in from ½ to 3 days from re-start up. Although not illustrated in Table 2 or FIG. 2, the activity of the catalyst also recovers to its pre-upset level in the same time frame of from ½ to 3 days.). The stability of the catalyst is increased as compared to a second supported silver catalyst comprised of the same materials except that the second catalyst does not contain at least one second promoter selected from the group consisting of sodium, lithium, and mixtures thereof.

TABLE VI

Data Plotted in FIG. 2

| Time On Stream [Days of Operation] | Cumulative EO Production [thousand kg/m³] | Selectivity [%] |
| --- | --- | --- |
| 33 | 132 | 82.7 |
| 34 | 136 | 82.7 |

TABLE VI-continued

Data Plotted in FIG. 2

| Time On Stream [Days of Operation] | Cumulative EO Production [thousand kg/m$^3$] | Selectivity [%] |
|---|---|---|
| 35 | 140 | 82.7 |
| 36 | 145 | 82.4 |
| 37 | 149 | 82.5 |
| 38 | 153 | 82.4 |
| 39 | 157 | 82.4 |
| 40 | 161 | 82.5 |
| 41 | 165 | 82.5 |
| 42 | 169 | 82.5 |
| 43 | 173 | 82.4 |
| 44 | 177 | 82.4 |
| 45 | 182 | 82.5 |
| 46 | 186 | 82.5 |
| 47 | 190 | 82.6 |
| 48 | 194 | 82.6 |
| 49 | 198 | 82.6 |
| 50 | 202 | 82.6 |
| 51 | 206 | 82.6 |
| 52 | 211 | 82.6 |
| 53 | 215 | 82.6 |
| 54 | 219 | 82.5 |
| 55 | 223 | 82.5 |
| 56 | 227 | 82.5 |
| 57 | 231 | 82.4 |
| 58 | 236 | 82.4 |
| 59 | 240 | 82.4 |
| 60 | 244 | 82.3 |
| 61 | 248 | 82.4 |
| 62 | 252 | 82.5 |
| 63 | 256 | 82.5 |
| 64 | 261 | 82.3 |
| 65 | 265 | 82.4 |
| 66 | 269 | 82.4 |
| 67 | 273 | 82.4 |
| 68 | 277 | 82.4 |
| 69 | 282 | 82.4 |
| 70 | 286 | 82.4 |
| 71 | 290 | 82.4 |
| 72 | 294 | 82.4 |
| 73 | 298 | 82.4 |
| 74 | 302 | 82.3 |
| 75 | 307 | 82.4 |
| 76 | 311 | 82.4 |
| 77 | 315 | 82.4 |
| 78 | 319 | 82.4 |
| 79 | 323 | 82.4 |
| 80 | 327 | 82.4 |
| 81 | 331 | 82.3 |
| 82 | 336 | 82.3 |
| 83 | 340 | 82.3 |
| 84 | 344 | 82.3 |
| 85 | 348 | 82.2 |
| 86 | 352 | 82.2 |
| 87 | 356 | 82.3 |
| 88 | 361 | 82.0 |
| 89 | 365 | 81.9 |
| 90 | 369 | 81.9 |
| 91 | 373 | 82.0 |
| 92 | 377 | 82.2 |
| 93 | 381 | 82.1 |
| 94 | 386 | 82.0 |
| 95 | 390 | 81.9 |
| 96 | 394 | 82.0 |
| 97 | 398 | 81.6 |
| 98 | 402 | 81.7 |
| 99 | 406 | 81.7 |
| 100 | 410 | 82.2 |
| 101 | 414 | 82.2 |
| 102 | 418 | 82.2 |
| 103 | 422 | 82.2 |
| 104 | 426 | 82.1 |
| 105 | 430 | 82.0 |
| 106 | 434 | 81.9 |
| 107 | 438 | 81.9 |
| 108 | 439 | 81.6 |
| 109 | 443 | 81.9 |
| 110 | 447 | 82.0 |
| 111 | 451 | 82.0 |
| 112 | 456 | 81.9 |
| 113 | 460 | 81.9 |
| 114 | 464 | 81.9 |
| 115 | 468 | 81.9 |
| 116 | 472 | 81.9 |
| 117 | 476 | 81.9 |
| 118 | 481 | 81.9 |
| 119 | 485 | 81.9 |
| 120 | 489 | 81.9 |
| 121 | 493 | 81.9 |
| 122 | 497 | 81.9 |
| 123 | 501 | 81.9 |
| 124 | 506 | 81.8 |
| 125 | 510 | 81.9 |
| 126 | 514 | 81.7 |
| 127 | 518 | 81.7 |
| 128 | 522 | 81.7 |
| 129 | 526 | 81.9 |
| 130 | 531 | 81.9 |
| 131 | 535 | 81.8 |
| 132 | 539 | 81.8 |
| 133 | 543 | 81.8 |
| 134 | 547 | 81.8 |
| 135 | 551 | 81.8 |
| 136 | 556 | 81.8 |
| 137 | 560 | 81.6 |
| 138 | 564 | 81.6 |
| 139 | 568 | 81.6 |
| 140 | 572 | 81.7 |
| 141 | 576 | 81.7 |
| 142 | 581 | 81.8 |
| 143 | 585 | 81.7 |
| 144 | 589 | 81.7 |
| 145 | 593 | 81.8 |
| 146 | 597 | 81.8 |
| 147 | 601 | 81.7 |
| 148 | 606 | 81.7 |
| 149 | 610 | 81.8 |
| 150 | 614 | 81.7 |
| 151 | 618 | 81.7 |
| 152 | 622 | 81.7 |
| 153 | 627 | 81.8 |
| 154 | 631 | 81.7 |
| 155 | 635 | 81.7 |
| 156 | 639 | 81.7 |
| 157 | 643 | 81.7 |
| 158 | 647 | 81.6 |
| 159 | 652 | 81.7 |
| 160 | 656 | 81.8 |
| 161 | 660 | 81.7 |
| 162 | 664 | 81.8 |
| 163 | 668 | 81.7 |
| 164 | 672 | 81.6 |
| 165 | 677 | 81.5 |
| 166 | 681 | 81.6 |
| 167 | 685 | 81.5 |
| 168 | 689 | 81.4 |
| 169 | 693 | 81.7 |
| 170 | 697 | 81.7 |
| 171 | 701 | 81.7 |
| 172 | 706 | 81.6 |
| 173 | 710 | 81.6 |
| 174 | 714 | 81.6 |
| 175 | 718 | 81.5 |
| 176 | 722 | 81.6 |
| 177 | 726 | 81.6 |
| 178 | 731 | 81.6 |
| 179 | 735 | 81.5 |
| 180 | 739 | 81.5 |

Example 3

A previously used sample of Catalyst 3 (40 cm$^3$) is evaluated in a continuously-stirred tank reactor in the epoxidation of ethylene with oxygen to evaluate its resiliency.

The catalyst is operated for 12 days under the following process conditions: inlet gas in mole percent: approximately 0.5 percent ethane, 4 ppm (molar) ethyl chloride, 30 percent ethylene, 8 percent oxygen, 0 to 3 percent CO$_2$, total inlet flow, 0.32 m$^3$/h (11.3 SCFH for GHSV of 8,000/h, total inlet pressure, 2000 kPa (absolute, or 275 psig), temperature, 200-240° C. The catalyst sample is discharged. (Data for this 12 day run is not reflected in FIG. 3 or in Table VII below.)

The used sample is charged to a different continuously-stirred tank reactor. The catalyst is operated under the following process conditions:
inlet gas in mole percent: approximately 0.5 percent ethane, 3.5 ppm (molar) ethyl chloride, 30 percent ethylene, 8 percent oxygen, 6.5 percent CO$_2$, total inlet pressure, 2000 kPa (absolute, or 275 psig), temperature, 240-242° C.

The reactor is started up at a total inlet flow of 0.64 m$^3$/h (22.6 SCFH for GHSV of 16,000/h). The inlet flow is reduced to 0.51 m$^3$/h (18 SCFH) after 3 days. The reactor is shut down after 4 days, stays down for 24 hours and is restarted under the same operating conditions.

The efficiency (EO selectivity) of the catalyst as a function of cumulative ethylene oxide production, in thousand kg EO per cubic meter of reactor volume, is shown in Table 3 and depicted in FIG. 3. The stability of the catalyst is increased as compared to a second supported silver catalyst comprised of the same materials except that the second catalyst does not contain at least one second promoter selected from the group consisting of sodium, lithium, and mixtures thereof.

TABLE VII

| Time On Stream [Days of Operation] | Cumulative EO Production* [thousand kg/m$^3$] | Selectivity [%] |
|---|---|---|
| 4 | 76.1 | 79.9 |
| 5 | 78.9 | 79.8 |
| 6 | 82.9 | 79.9 |
| 7 | 87.1 | 79.7 |
| 8 | 91.2 | 79.7 |
| 9 | 94.9 | 79.8 |

*includes cumulative EO production from previous operation

Example 4

A stability study is performed upon a sample of Catalyst 2.

A sample of the catalyst (3.65 kg) is loaded into a fixed-bed reactor and evaluated in the epoxidation of ethylene with oxygen under the following process conditions:
  inlet gas in mole percent: 30 percent ethylene, 8.5 percent oxygen, 6.0 percent carbon dioxide, 0.6 percent ethane, 6.5 ppm (molar) ethyl chloride, and balance nitrogen; total inlet flow, 20 m$^3$/h (690 SCFH for GHSV of 3,550/h)
  total inlet pressure, 2,170 kPa (absolute, or 300 psig) temperature, 215-240° C.
The outlet effluent comprises 2.5 percent ethylene oxide (equivalent to a workrate of 4 kg-mol EO/h/m$^3$).

The selectivity and activity are monitored and recorded as is the cumulative ethylene oxide production and the inlet coolant temperature. After the catalyst has been fully activated, and for the period of approximately six months after the process is initiated, a plot of selectivity versus cumulative ethylene oxide production at a constant ethylene oxide production rate and a plot of inlet coolant temperature versus cumulative ethylene oxide production at a constant ethylene oxide production rate are prepared as described on page 6 of this application. The slopes are calculated as described on page 6. The aging rate of the catalyst is then compared to that of a second supported silver catalyst comprised of the same materials except that the second catalyst does not contain at least one second promoter selected from the group consisting of sodium, lithium, and mixtures thereof.

Example 5

An 80-cm3 sample of Catalyst 4 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After two days of operation, the reactor temperature is increased to 240° C. On the fourth day of operation, the inlet ethyl chloride concentration is decreased to 2 ppm, then changed to 4 ppm and then 3 ppm on the subsequent days. During the eleventh day of testing, the reactor experiences an unplanned emergency shutdown during which the catalyst charge is cooled down and maintained under a nitrogen atmosphere. On the third day following the shutdown, the catalyst is restarted under the same reaction conditions in use at the time of the shutdown.

On the day of the unplanned shutdown, the catalyst is producing approximately 2.20% EO with 85.1% selectivity at 240° C. On the first day following the restart, the catalyst activity averages approximately 2.13% EO at 83.7% selectivity, and on the second, third and fourth days following the restart, the catalyst produces 2.16, 2.17 and 2.18% EO, with efficiency of 85.0, 85.2 and 85.2%, respectively.

Between the seventh and twenty-second operating days of the run, a period spanning the unplanned shutdown and subsequent restart, the catalyst activity declines at an average rate of –0.017% EO/day.

The activity of the catalyst is monitored over time. The catalyst exhibits resilience, stability, as well as increased activity under the same process conditions of at least about 3° C. as compared with a second supported silver catalyst comprised of the same materials except that the second catalyst does not contain manganese.

Comparative Example 6

A sample of comparative Catalyst 5 (80 cm$^3$) is evaluated in a continuously-stirred tank reactor in the epoxidation of ethylene with oxygen to evaluate its resiliency.

The catalyst is operated for 30 days with 5 days shut down and 25 days under the following process conditions: inlet gas in mole percent: approximately 0.5 percent ethane, 3.5 ppm (molar) ethyl chloride, 30 percent ethylene, 8 percent oxygen, 6.5 percent CO$_2$, total inlet flow, 0.64 m$^3$/h (22.6 SCFH for GHSV of 8,000/h, total inlet pressure, 2000 kPa (absolute, or 275 psig), temperature, 200-240° C.

The reactor is started up at the total inlet flow of 0.64 m$^3$/h (22.6 SCFH for GHSV of 8,000/h) at 230° C. The temperature is gradually increased within 24 hours to reach the desired catalyst productivity. The productivity of the catalyst is maintained by increasing operating temperature as catalyst deactivates.

The efficiency (EO selectivity) of the catalyst as a function of cumulative ethylene oxide production, in thousand kg EO per cubic meter of reactor volume, is shown in Table VIII. The selectivity of the catalyst shows a step change loss after the shutdown.

TABLE VIII

| Time On Stream [Days of Operation] | Cumulative EO Production [thousand kg/m³] | Selectivity [%] |
|---|---|---|
| 1 | 4.8 | 81.25 |
| 2 | 11.2 | 79.73 |
| 3 | 17.6 | 79.59 |
| 4 | 23.9 | 79.54 |
| 5 | 30.2 | 79.53 |
| 6 | 36.5 | 79.52 |
| 7 | 42.8 | 79.56 |
| 8 | 49.2 | 79.58 |
| 9 | 55.1 | 79.58 |
| 10 | 55.1 | Shutdown |
| 11 | 55.1 | Shutdown |
| 12 | 55.1 | Shutdown |
| 13 | 55.1 | Shutdown |
| 14 | 55.1 | Shutdown |
| 15 | 63.9 | 78.81 |
| 16 | 70.2 | 79.06 |
| 17 | 76.6 | 79.08 |
| 18 | 82.9 | 79.12 |
| 19 | 89.2 | 79.05 |
| 20 | 95.6 | 78.78 |
| 21 | 101.9 | 78.72 |
| 22 | 108.3 | 78.74 |
| 23 | 114.6 | 78.74 |
| 24 | 120.9 | 78.63 |
| 25 | 127.3 | 78.54 |
| 26 | 133.6 | 78.43 |
| 27 | 138.9 | 78.35 |
| 28 | 145.2 | 78.14 |
| 29 | 151.5 | 78.04 |
| 30 | 157.3 | 77.91 |

Comparative Example 7

A sample (2287 g) of comparative Catalyst 6 is loaded into a fixed-bed reactor and evaluated in the epoxidation of ethylene with oxygen under the following process conditions:

inlet gas in mole percent: 30 percent ethylene, 8.5 percent oxygen, 6.0 percent carbon dioxide, 0.6 percent ethane, 4.6 ppm (molar) ethyl chloride, and balance nitrogen;

total inlet flow, 12.74 m3/hr (450 SCFH referenced to 0 C and 1 atm, absolute)

total inlet pressure, 2,170 kPa (absolute, or 300 psig)

temperature, 225-233° C.

The outlet effluent comprises 2.5 percent ethylene oxide (equivalent to a workrate of 4 kg-mol EO/h/m³). The ethylene oxide efficiency (EO selectivity) of the catalyst is tabulated in Table IX as a function of cumulative EO production, in thousand kg EO produced per cubic meter of reactor volume, and the time on stream (in days of operation, not necessarily consecutive calendar days). Each data point in Table IX is a daily (24 h) average of catalyst efficiency. Restart of the reactor after a shutdown occurred on Days 38, 44, 69, 77, 99 and 122.

TABLE IX

| Time On Stream [Days of Operation] | Cumulative EO Production [thousand kg/m³] | Selectivity [%] |
|---|---|---|
| 21 | 92 | 82.16 |
| 22 | 97 | 81.90 |
| 23 | 101 | 82.22 |
| 24 | 105 | 82.25 |
| 25 | 110 | 82.34 |
| 26 | 114 | 81.97 |
| 27 | 119 | 81.52 |
| 28 | 124 | 81.54 |
| 31 | 128 | 82.12 |
| 32 | 133 | 82.09 |
| 33 | 137 | 82.12 |
| 34 | 141 | 82.21 |
| 37 | 146 | 82.10 |
| 38* | 150 | 82.16 |
| 39 | 154 | 82.16 |
| 40 | 159 | 82.05 |
| 41 | 163 | 82.09 |
| 42 | 167 | 82.05 |
| 43 | 172 | 81.73 |
| 44* | 176 | 80.47 |
| 45 | 180 | 80.92 |
| 46 | 185 | 80.88 |
| 47 | 189 | 80.63 |
| 48 | 193 | 80.96 |
| 49 | 198 | 81.17 |
| 50 | 202 | 81.29 |
| 51 | 206 | 81.52 |
| 52 | 211 | 81.59 |
| 53 | 215 | 81.61 |
| 54 | 219 | 81.52 |
| 55 | 224 | 81.51 |
| 56 | 228 | 81.51 |
| 57 | 232 | 81.47 |
| 58 | 237 | 81.52 |
| 59 | 241 | 81.47 |
| 60 | 245 | 81.59 |
| 61 | 250 | 81.51 |
| 65 | 267 | 80.87 |
| 66 | 271 | 80.90 |
| 67 | 276 | 81.11 |
| 68 | 280 | 81.45 |
| 72* | 297 | 80.25 |
| 73 | 302 | 80.28 |
| 74 | 306 | 80.46 |
| 75 | 310 | 80.79 |
| 76 | 315 | 81.45 |
| 79* | 327 | 80.69 |
| 80 | 331 | 80.71 |
| 81 | 335 | 80.71 |
| 82 | 340 | 80.92 |
| 83 | 344 | 81.04 |
| 84 | 348 | 80.96 |
| 85 | 353 | 80.81 |
| 86 | 357 | 80.76 |
| 87 | 362 | 80.26 |
| 88 | 366 | 80.30 |
| 89 | 370 | 80.26 |
| 90 | 375 | 80.40 |
| 91 | 379 | 80.21 |
| 92 | 383 | 80.42 |
| 93 | 388 | 80.50 |
| 98 | 410 | 79.13 |
| 99* | 414 | 79.41 |
| 100 | 418 | 79.84 |
| 101 | 423 | 79.99 |
| 102 | 427 | 79.80 |
| 103 | 431 | 80.31 |
| 104 | 436 | 80.34 |
| 105 | 440 | 80.22 |
| 106 | 444 | 80.15 |
| 107 | 449 | 80.15 |
| 108 | 453 | 80.29 |
| 109 | 457 | 80.31 |
| 110 | 462 | 80.25 |
| 111 | 466 | 80.05 |
| 112 | 470 | 79.98 |
| 113 | 475 | 80.05 |

TABLE IX-continued

| Time On Stream [Days of Operation] | Cumulative EO Production [thousand kg/m³] | Selectivity [%] |
|---|---|---|
| 114 | 479 | 79.96 |
| 115 | 484 | 80.18 |
| 116 | 488 | 80.29 |
| 117 | 492 | 80.48 |
| 118 | 497 | 80.48 |
| 119 | 501 | 80.44 |
| 120 | 505 | 80.47 |
| 121 | 510 | 80.50 |
| 122* | 514 | 80.53 |
| 123 | 518 | 80.53 |
| 124 | 523 | 80.60 |
| 125 | 527 | 80.62 |
| 126 | 531 | 80.56 |
| 127 | 536 | 80.59 |
| 128 | 540 | 80.57 |

Comparative Example 8

A 40-cm3 sample of Comparative Catalyst 7 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 11.3 SCFH (0.32 m3/h, 8000 gas-hourly space velocity), reactor temperature of 230° C.

After two days of operation, the reactor temperature is increased to 240° C. and held at this level for the remainder of the run. On the next day of testing, the inlet ethyl chloride concentration is decreased to 2 ppm, then changed to 2.5 ppm on the following day (Day 5). This ethyl chloride concentration is maintained through Day 13 of the test. On Day 5, the catalyst performance averages 2.12% EO at 83.6% selectivity. On Day 11, the averages are 1.98% EO and 84.0%. On Day 13, the activity is 1.88% EO and the selectivity is 84.6%. A linear regression of the activity measured between Days 5 and 13 shows an average decline rate of −0.029% EO/day.

Example 9

An evaluation of Catalyst 8 is conducted in parallel with that of Catalyst 4 (Example 5), using the same type of continuously-stirred tank reactor and the same test protocol through the first fifteen days of operation.

During the eleventh day of testing, just as in Example 5, the reactor experiences an unplanned emergency shutdown during which the catalyst charge is cooled down and maintained under a nitrogen atmosphere. On the third day following the shutdown, Catalyst 8 is restarted under the same reaction conditions in use at the time of the shutdown.

By the end of the second day following the restart, Catalyst 8 regains 93% of the activity observed prior to the unplanned shutdown while the selectivity increases by 0.1 percentage points. That is, the % EO in the outlet stream from the reactor reaches 93% of the concentration present on the day of the emergency shutdown.

Example 10

A 80-cm³ sample of Catalyst 9 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 2 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After two days of operation, the reactor temperature is increased to 240° C. and held there for the remainder of the test. On the fifth day of operation, the inlet ethyl chloride concentration is increased to 3 ppm for two days, then returned to 2 ppm. From Day 7 to 43 of operation, the ethyl chloride concentration is adjusted between about 2 and 3.5 ppm for varying lengths of time in order to evaluate catalyst activity, efficiency and stability. On Day 18, at 2.5 ppm ethyl chloride, the catalyst produces 1.77% EO with a selectivity of 87.1%.

From Day 44 to 67, the inlet ethyl chloride concentration is maintained at 3.0 ppm with the exception of Days 51 and 65, when the concentration is 3.2 ppm. During this period, the average decline rate for activity as determined by linear regression is −0.0027% EO/day while that for selectivity is −0.013 percentage points/day.

Example 11

A 80-cm³ sample of Catalyst 10 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

For the second day of operation, the reactor temperature is increased to 240° C. For the third day, the inlet ethyl chloride concentration is decreased to 2 ppm. During the third day, the reactor undergoes an unplanned shutdown and is restarted the following day under the same conditions. For the two hours preceding the shutdown, Catalyst 10 is producing an average of 1.76% EO. During the twenty-second hour after the restart, the catalyst activity averages 1.75% EO.

Over the next four days of testing, the inlet ethyl chloride concentration is adjusted between 1.5 and 2.7 ppm. On Day 12, at 2.7 ppm ethyl chloride, the catalyst produces 1.70% EO with 88.0% selectivity.

Example 12

A 80-cm3 sample of Catalyst 11 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After two days of operation, the reactor temperature is increased to 240° C. On the next day, the inlet ethyl chloride concentration is decreased to 2 ppm for two days. Over the next five days, the ethyl chloride level is adjusted between about 1.5 and 4 ppm. On Day 10, at 2 ppm ethyl chloride, Catalyst 11 produces 2.07% EO with a selectivity of 84.7%.

Example 13

A 80-cm3 sample of Catalyst 12 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After one day of operation, the reactor temperature is increased to 240° C. On the next day, the inlet ethyl chloride concentration is decreased to 2 ppm for two days. From Day 5 through 15, the inlet ethyl chloride concentration is held at various levels between 1.5 and 4 ppm for one to three days at a time. After Day 15, the intervals between changes in ethyl chloride concentration are generally lengthened.

On Day 65, at 3.4 ppm ethyl chloride, Catalyst 12 produces 1.46% EO at 86.7% efficiency. Between Days 65 and 105, except for the first two days of operation following an unplanned shutdown during Day 86, the ethyl chloride concentration is maintained at levels between about 3.4 and 3.5 ppm. During this period, the average activity decline rate is −0.0011% EO/day while the corresponding rate for selectivity is −0.017 percentage points/day.

Example 14

A 80-cm3 sample of Catalyst 13 is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 3 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After one day of operation, the reactor temperature is increased to 240° C. On the next day, the inlet ethyl chloride concentration is decreased to 2 ppm for two days. From Day 5 through 13, the inlet ethyl chloride concentration is adjusted to levels between 1.5 and 4 ppm for one to three days at a time. After Day 13, the intervals between further ethyl chloride adjustments are generally lengthened.

On Day 34 of operation, Catalyst 13 undergoes an unplanned shutdown. Just before the shutdown, at an ethyl chloride concentration of about 2.6 ppm, the catalyst is producing 1.64% EO with 85.4% selectivity. Eighteen hours after the catalyst is restarted under the same conditions, the catalyst produces 1.65% EO with 85.4% selectivity.

Example 15

Using the same carrier and procedures as employed in Example 5, Catalyst 14 is prepared with the same target promoter concentrations. The finished catalyst is calculated to contain the following amounts of deposited components: 36.47 wt % silver, 526 ppm cesium, 28 ppm lithium, 34 ppm sodium, 368 ppm rhenium, 131 ppm sulfate and 109 ppm manganese, all based on the weight of the catalyst.

A 80-cm3 sample of this catalyst is evaluated in a continuously-stirred tank reactor in the epoxidation of ethylene with oxygen. The catalyst is started up under the following process conditions: 30% ethylene, 8% oxygen, 3% carbon dioxide, 0.5% ethane, 2 ppm ethyl chloride, balance nitrogen, all measured as inlet concentrations, 275 psig (2000 kPa, absolute), inlet gas flow of 22.6 SCFH (0.64 m3/h, 8000 gas-hourly space velocity), reactor temperature of 230° C.

After one day of operation, the reactor temperature is increased to 240° C. Two days later, the inlet ethyl chloride concentration is increased to 4 ppm, then lowered to 3 ppm and 2 ppm on the following days. On Day 6, at 2 ppm ethyl chloride, the catalyst averages 2.18% EO at a selectivity of 85.8%.

In a separate test, an unused sample of this catalyst is charged to a fixed-bed reactor and is evaluated under a variety of different process conditions. This reactor is configured such that a portion of the outlet gas is recycled, following removal of ethylene oxide in an absorber unit, to form part of the feed gas to the reactor inlet. At a cumulative production of about 22.5 thousand lb EO/ft3 catalyst (0.36 kT EO per $m^3$ catalyst), the catalyst is producing 2.20% EO with a selectivity of 88.1% at a reactor coolant temperature (top shell temperature) of 233.3° C. under the following process conditions: 30% ethylene, 8.5% oxygen, 2% carbon dioxide, 0.6% ethane, 4.2 ppm ethyl chloride (optimum for selectivity), balance nitrogen, all measured as inlet concentrations, 295 psig (2140 kPa, absolute), 5700 gas-hourly space velocity.

Using a proprietary model for predicting the performance of an epoxidation catalyst under different operating conditions, at 2% carbon dioxide but with lowered inlet ethylene and oxygen concentrations of 25% and 8%, respectively, 315 psig (2270 kPa, absolute), and 4700 gas-hourly space velocity, the catalyst produces 2.00% EO with 87.6% selectivity at a temperature of 230.5° C., corresponding to a productivity of 11.5 lb EO/ft3/hr (184 kg EO per $m^3$ per hour).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon the foregoing description. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A supported silver catalyst prepared on an alumina-containing carrier, the carrier comprising greater than about 95 weight percent alpha-alumina and less than about 30 parts per million acid-leachable alkali metals by weight, the weight percent of the alumina and the concentration of the acid-leachable alkali metals being calculated on the weight of the carrier, wherein the acid-leachable alkali metals are selected from lithium, sodium, potassium, and mixtures thereof, the carrier having deposited thereon:
   (A) silver in an amount greater than about 25 weight percent, based on the weight of the catalyst;
   (B) cesium as a first promoter in an amount from about 200 ppm to about 1200 ppm by weight;
   (C) sodium in an amount from about 10 ppm to about 150 ppm by weight;
   (D) lithium in an amount from about 10 ppm to about 100 ppm by weight, and optional additional solid promoters;
   the concentrations of the deposited sodium, lithium, and optional additional solid promoters being calculated on the weight of the catalyst.

2. The supported silver catalyst of claim 1, wherein the alpha-alumina carrier consists essentially of greater than about 98 weight percent alpha-alumina and less than about 30 ppm acid-leachable lithium, sodium, and potassium by weight; the weight percent of the alumina and the concentration of the acid-leachable alkali metals being calculated on the weight of the carrier; and the carrier further has deposited thereon manganese in an amount from about 20 ppm to about 200 ppm by weight; and a promoting amount of sulfur compound and, optionally, rhenium, tungsten, molybdenum, or mixtures thereof, wherein the ratio of 2(moles sulfur plus moles tungsten plus moles molybdenum) plus moles rhenium divided by the total moles cesium and sodium [(2(S+W+Mo)+Re)/(Cs+Na)] ranges from greater than about 0.5/1 to about 1.5/1.

3. The supported silver catalyst of claim 1, further comprising a promoting amount of sulfur compound and, optionally, rhenium, tungsten, molybdenum, or mixtures thereof, wherein the ratio of 2(moles sulfur plus moles tungsten plus moles molybdenum) plus moles rhenium divided by the total moles cesium and sodium [(2(S+W+Mo)+Re)/(Cs+Na)] ranges from greater than about 0.5/1 to about 1.5/1.

4. The supported silver catalyst of claim 1, wherein the catalyst comprises a synergistic combination of cesium, sodium, and lithium when used as a catalyst for the production of ethylene oxide.

5. The supported silver catalyst of claim 1 further comprising a promoting amount of rhenium.

6. The supported silver catalyst of claim 1 further comprising a promoting amount of manganese.

7. The supported silver catalyst of claim 1 further comprising a promoter selected from compounds of sulfur, molybdenum, tungsten, and mixtures thereof.

8. The supported silver catalyst of claim 2, wherein the amount of manganese is at least about 1.5 micromoles per gram of catalyst.

9. The supported catalyst of claim 1 wherein the alumina-containing support comprises particles of alpha-alumina each of which has at least one substantially flat major surface having a lamellate or platelet morphology which approximates the shape of a hexagonal plate, at least 50 percent of which (by number) have a major dimension of less than about 50 microns.

10. The supported silver catalyst of claim 2 wherein the catalyst is capable of producing ethylene oxide at a selectivity of at least 87 percent while achieving a work rate of at least 184 kg/h/m$^3$ of catalyst at a temperature of no greater than 235° C. when operated in a process using a reactor containing the catalyst, the reactor being provided with an inlet feed and having withdrawn therefrom an outlet stream, where the inlet feed to a reactor containing the catalyst comprises ethylene, oxygen, and carbon dioxide, wherein the concentration of carbon dioxide in the inlet feed is greater than or equal to 2 mole percent.

11. The supported silver catalyst of claim 2, wherein the catalyst is capable of producing ethylene oxide at a selectivity of at least 87 percent while achieving a work rate of at least 184 kg/h/m$^3$ of catalyst at a temperature of no greater than 240° C. when operated in a process using a reactor containing the catalyst, the reactor being provided with an inlet feed and having withdrawn therefrom an outlet stream, where the inlet feed to the reactor comprises ethylene, oxygen, and carbon dioxide, wherein the concentration of carbon dioxide in the inlet feed is greater than or equal to 2 mole percent and at least a portion of the carbon dioxide has been recycled from the outlet stream of the reactor.

12. A process for producing a supported silver catalyst, the process comprising:
   (a) providing an alumina-containing carrier, the carrier comprising greater than about 95 weight percent alpha-alumina and less than about 30 parts per million acid-leachable alkali metals by weight, the weight percent of the alumina and the concentration of the acid-leachable alkali metals being calculated on the weight of the carrier, wherein the acid-leachable alkali metals are selected from lithium, sodium, potassium, and mixtures thereof; and
   (b) depositing on the carrier:
      (A) silver in an amount greater than about 25 weight percent, based on the weight of the catalyst;
      (B) cesium as a first promoter in an amount from about 200 ppm to about 1200 ppm by weight;
      (C) sodium in an amount from about 10 ppm to about 150 ppm by weight;
      (D) lithium in an amount from about 10 ppm to about 100 ppm by weight, and optionally, additional solid promoters; the concentrations of the deposited sodium lithium and optional additional solid promoters being calculated on the weight of the catalyst.

* * * * *